US005486463A

United States Patent [19]

[11] Patent Number: 5,486,463

Lesslauer et al.

[45] Date of Patent: Jan. 23, 1996

[54] TNF-MUTEINS

[75] Inventors: Werner Lesslauer, Riehen; Hansruedi Lötscher, Mölin, both of Switzerland; Dietrich Stüber, Grenzach-Wyhlen, Germany

[73] Assignee: Hoffmann-La Roche Inc., Nutley, N.J.

[21] Appl. No.: 41,648

[22] Filed: Apr. 1, 1993

[30] Foreign Application Priority Data

Apr. 2, 1992 [EP] European Pat. Off. .............. 92810249

[51] Int. Cl.$^6$ .......................... C12P 21/06; C07H 17/00; C07K 14/00; C12N 1/20

[52] U.S. Cl. .................... 435/69.5; 536/23.5; 536/23.51; 530/351; 435/252.33; 435/320.1

[58] Field of Search .......................... 530/351; 435/69.5, 435/320.1, 106; 536/23.5, 123.5

[56] References Cited

U.S. PATENT DOCUMENTS 4,948,875 8/1990 Tanaka et al. .

OTHER PUBLICATIONS

Goh and Porter, "Structural and functional domains in human tumour necrosis factors", Protein Engineering 4:385–389 (1991).

Fiers, "INF: Mechanism of Action in Vitro and in Vivo", in Influence of Molecular Biology on Drug Discovery, ed. Udaka et al. (Munich, W. Zuckerschwerdt Verlag 1989) pp. 17–24.

Fiers, "Precursor Structures and Structure/Function Analysis of TNF and Lymphotoxin", in Tumor Necrosis Factors: Structure, Function and Mechanism of Action, ed. Aggarwal and Vilcek (Marcel Dekker, New York 1992), pp. 79–92.

Yamagishi et al., Protein Engineering 3:713–719 (1990), "Mutational analysis of structure—activity relationships in human tumor necrosis factor–alpha".

Van Ostade et al., EMBO J. 10:827–836 (1991) "Localization of the active site of human tumour necrosis factor (hTNF) by mutational analysis".

Fiers et al., "In vitro and in vivo action of tumor necrosis factor", in Tumor Necrosis Factor: Structure, Mechanism of Action, Role in Disease and Therapy, ed. Bonavida and Granger, (S. Karger, Basel, 1990), pp. 77–81.

Mackay et al, J. Exp. Med. 177:1277–1286 (1993), "Tumor necrosis factor α (TNF–60 )—Induced cell adhesion to human endothelial cells in under dominant control of one TNF receptor type, TNF–R55".

Loetscher et al., J. Biol. Chem. (in press, 1993), "Human tumor necrosis factor α(TNFα) muteins with exclusive specificity for the 55 kDA or 75 kDa TNF receptors".

Loetscher et al., (1993) 8th Symposium Molecular Biology Hematopoiesis, Basel, Jul. 9–13 (Manuscript No. B 161 605) "Activation of TNF receptors: structural and functional aspects".

Angehrn et al., "Two distinct tumor necrosis factor receptors in Health and disease", in Tumor Necrosis Factor: Molecular and Cellular Biology and Clinical Relevance, ed. Fiers & Buurman (Karger, Basel (1993) pp. 33–39.

Lesslauer et al., "Cell–associated and soluble TNF receptors: perspectives of new therapeutic strategies", in Maurice Rapin Colloquia Mediators of Sepsis: From Pathophysiology to Therapeutic Approaches (Manuscript No. 161 230) (Paris, Flammarion in press 1993).

Fiers et al., "Lymphokines and monokines in Anti–cancer Therapy", in Cold Spring Harbor Symposium on Quatitative Biology, vol. LI (Cold Spring Harbor, 1986) pp. 587–595.

Tartaglia et al. 1993 Cell 73:213–216.

Ostade, et al., "Human TNF mutants with selective activity on the p. 55 receptor", Nature 361, 266–269 (1993).

Warren, et al. "The Acute Metabolic Effects of Tumor Necrosis Factor Administration in Humans", Arch Surg, 122 1396–1400 (1987).

Taguchi, et al., "Clinical Studies with TNF", Biotherapy 3, 177–186 (1991).

Brouckaert, et al., "In Vivo Anti–Tumour Activity of Recombinant Human And Murine TNF, Alone and in Combination with Murine IFN–65, On A Syngeneic Murine Melanoma", Int. J. Cancer 38, 763–769 (1986).

Styer 1981. Biochemistry. WH Freemane and Co. San Francisco.

Pennica et al. 1984 Nature 312:724.

*Primary Examiner*—Garnette D. Draper
*Assistant Examiner*—K. Cochrane Carlson
*Attorney, Agent, or Firm*—George M. Gould; William H. Epstein; Catherine A. Picut

[57] ABSTRACT

The present invention is directed to a human Tumor Necrosis Factor mutein or a pharmaceutically acceptable salt thereof having selective binding affinity for the human p55-Tumor-Necrosis-Factor-Receptor characterized in that the amino acid sequence of human Tumor Necrosis Factor is changed at least at position 86 having a threonine instead of a serine residue, a DNA sequence coding for such a mutein, a vector comprising such a DNA sequence, and a host cell transformed by such a vector.

27 Claims, 15 Drawing Sheets

```
       XhoI
1    CTCGAGAAAT  CATAAAAAAT  TTATTTGCTT  TGTGAGCGGA  TAACAATTAT
                                                      EcoRI
51   AATAGATTCA  ATTGTGAGCG  GATAACAATT  TCACACAGAA  TTCATTAAAG

101  AGGAGAAATT  AAGCATGGTC  AGATCATCTT  CTCGAACCCC  GAGTGACAAG
                        Val  ArgSerSerS  erArgThrPr  oSerAspLys
                        1                                    11
151  CCTGTAGCCC  ATGTTGTCGC  GAACCCTCAA  GCTGAGGGGC  AGCTCCAGTG
     ProValAlah  isValValAl  aAsnProGln  AlaGluGlyG  lnLeuGlnTr
                             BglI  21
201  GCTGAACCGA  CGGGCCAATG  CCCTCCTGGC  CAATGGCGTG  GAGCTGAGAG
     pLeuAsnArg  ArgAlaAsnA  laLeuLeuAl  aAsnGlyVal  GluLeuArgA
             31                                  41
251  ATAACCAGCT  GGTGGTGCCA  TCAGAGGGCC  TGTACCTCAT  CTACTCCCAG
     spAsnGlnLe  uValValPro  SerGluGlyL  euTyrLeuIl  eTyrSerGln
                         51                                  61
301  GTCCTCTTCA  AGGGCCAAGG  CTGCCCCTCC  ACCCATGTGC  TCCTCACCCA
     ValLeuPheL  ysGlyGlnGl  yCysProSer  ThrHisValL  euLeuThrHi
                                     71
351  CACCATCAGC  CGCATCGCCG  TCTCCTACCA  GACCAAGGTC  AACCTCCTCT
     sThrIleSer  ArgIleAlaV  alSerTyrGl  nThrLysVal  AsnLeuLeuS
             81                                  91
401  CTGCCATCAA  GAGCCCCTGC  CAGAGGGAGA  CCCCAGAGGG  GGCTGAGGCC
     erAlaIleLy  sSerProCys  GlnArgGluT  hrProGluGl  yAlaGluAla
                        101                                 111
451  AAGCCCTGGT  ATGAGCCCAT  CTATCTGGGA  GGGGTCTTCC  AGCTGGAGAA
     LysProTrpT  yrGluProIl  eTyrLeuGly  GlyValPheG  lnLeuGluLy
                                    121
501  GGGTGACCGA  CTCAGCGCTG  AGATCAATCG  GCCCGACTAT  CTCGACTTTG
     sGlyAspArg  LeuSerAlaG  luIleAsnAr  gProAspTyr  LeuAspPheA
            131                                 141
551  CCGAGTCTGG  GCAGGTCTAC  TTTGGGATCA  TTGCCCTGTG  AGGAGGACGA
     laGluSerGl  yGlnValTyr  PheGlyIleI  leAlaLeu
                        151                157
601  ACATCCAACC  TTCCCAAACG  CCTCCCCTGC  CCCAATCCCT  TTATTACCCC

651  CTCCTTCAGA  CACCCTCAAC  CTCTTCTGGC  TCAAAAAGAG  AATTGGGGGC
                  HindIII
701  TTAGGGTCGG  AACCCAAGCT  TGGACTCCTG  TTGATAGATC  CAGTAATGAC

751  CTCAGAACTC  CATCTGGATT  TGTTCAGAAC  GCTCGGTTGC  CGCCGGGCGT
```

FIG. 1b-1

801 TTTTTATTGG TGAGAATCCA AGCTAGCTTG GCGAGATTTT CAGGAGCTAA

851 GGAAGCTAAA ATGGAGAAAA AAATCACTGG ATATACCACC GTTGATATAT

901 CCCAATGGCA TCGTAAAGAA CATTTTGAGG CATTTCAGTC AGTTGCTCAA

951 TGTACCTATA ACCAGACCGT TCAGCTGGAT ATTACGGCCT TTTTAAAGAC

001 CGTAAAGAAA AATAAGCACA AGTTTTATCC GGCCTTTATT CACATTCTTG

051 CCCGCCTGAT GAATGCTCAT CCGGAATTTC GTATGGCAAT GAAAGACGGT

101 GAGCTGGTGA TATGGGATAG TGTTCACCCT TGTTACACCG TTTTCCATGA

151 GCAAACTGAA ACGTTTTCAT CGCTCTGGAG TGAATACCAC GACGATTTCC

201 GGCAGTTTCT ACACATATAT TCGCAAGATG TGGCGTGTTA CGGTGAAAAC

251 CTGGCCTATT TCCCTAAAGG GTTTATTGAG AATATGTTTT TCGTCTCAGC

301 CAATCCCTGG GTGAGTTTCA CCAGTTTTGA TTTAAACGTG GCCAATATGG

351 ACAACTTCTT CGCCCCCGTT TTCACCATGG GCAAATATTA TACGCAAGGC

401 GACAAGGTGC TGATGCCGCT GGCGATTCAG GTTCATCATG CCGTCTGTGA

451 TGGCTTCCAT GTCGGCAGAA TGCTTAATGA ATTACAACAG TACTGCGATG

501 AGTGGCAGGG CGGGGCGTAA TTTTTTTAAG GCAGTTATTG GTGCCCTTAA

551 ACGCCTGGGG TAATGACTCT CTAGCTTGAG GCATCAAATA AAACGAAAGG

601 CTCAGTCGAA AGACTGGGCC TTTCGTTTTA TCTGTTGTTT GTCGGTGAAC

XbaI

1651 GCTCTCCTGA GTAGGACAAA TCCGCCGCTC TAGAGCTGCC TCGCGCGTTT

1701 CGGTGATGAC GGTGAAAACC TCTGACACAT GCAGCTCCCG GAGACGGTCA

1751 CAGCTTGTCT GTAAGCGGAT GCCGGGAGCA GACAAGCCCG TCAGGGCGCG

1801 TCAGCGGGTG TTGGCGGGTG TCGGGGCGCA GCCATGACCC AGTCACGTAG

1851 CGATAGCGGA GTGTATACTG GCTTAACTAT GCGGCATCAG AGCAGATTGT

1901 ACTGAGAGTG CACCATATGC GGTGTGAAAT ACCGCACAGA TGCGTAAGGA

1951 GAAAATACCG CATCAGGCGC TCTTCCGCTT CCTCGCTCAC TGACTCGCTG

2001 CGCTCGGTCT GTCGGCTGCG GCGAGCGGTA TCAGCTCACT CAAAGGCGGT

2051 AATACGGTTA TCCACAGAAT CAGGGGATAA CGCAGGAAAG AACATGTGAG

2101 CAAAAGGCCA GCAAAAGGCC AGGAACCGTA AAAAGGCCGC GTTGCTGGCG

FIG. 1b-2

2151 TTTTTCCATA GGCTCCGCCC CCCTGACCAG CATCACAAA ATCGACGCTC

2201 AAGTCAGAGG TGGCGAAACC CGACAGGACT ATAAAGATAC CAGGCGTTC

2251 CCCCTGGAAG CTCCCTCGTG CGCTCTGCTG TTCCGACCCT GCCGCTTACC

2301 GGATACCTGT CCGCCTTTCT CCCTTCGGGA AGCGTGGCGC TTTCTCAATG

2351 CTCACGCTGT AGGTATCTCA GTTCGGTGTA GGTCGTTCGC TCCAAGCTGG

2401 GCTGTGTGCA CGAACCCCCC GTTCAGCCCG ACCGCTGCGC CTTCTCCGGT

2451 AACTATCGTC TTGAGTCCAA CCCGGTAAGA CACGACTTAT CGCCACTGGC

2501 AGCAGCCACT GGTAACAGGA TTAGCAGAGC GAGGTATGTA GGCGGTGCTA

2551 CAGAGTTCTT GAAGTGGTGG CCTAACTACG GCTACACTAG AAGGACAGTA

2601 TTTGGTATCT GCGCTCTGCT GAAGCCAGTT ACCTTCGGAA AAAGAGTTGG

2651 TAGCTCTTGA TCCGGCAAAC AAACCACCGC TGGTAGCCGT GGTTTTTTTG

2701 TTTGCAAGCA GCAGATTACG CGCAGAAAAA AAGGATCTCTA AGAAGATTCCT

2751 TTGATCTTTT CATCGGGGTC TGACGCTCAG TGGAACGAAA ACTCACGTTA

2801 AGGGATTTTG GTCATGAGAT TATCAAAAAG GATCTTCACC TAGATCCTTT

2851 TAAATTAAAA ATGAAGTTTT AAATCAATCT AAAGTATATA TGAGTAAACT

2901 TGGTCTGACA GTTACCAATG CTTAATCAGT GAGGCACCTA TCTCAGCGAT

2951 CTGTCTATTT CGTTCATCCA TAGCTGCCTG ACTCCCCGTC GTGTAGATAA

3001 CTACGATACG GGAGGGCTTA CCATCTGGCC CCAGTGCTGC AATGATACCG

3051 CGAGACCCAC GCTCACCGGC TCCAGATTTA TCCAGATTTA ACCAGCCAGC

BglI

3101 CGGAAGGGCC GAGCGCAGAA GTGGTCCTGC AACTTTATCC GCCTCCATCC

3151 AGTCTATTAA TTGTTGCCGG GAAGCTAGAG TAAGTAGTTC GCCAGTTAAT

3201 AGTTTGCGCA ACGTTGTTGC CATTGCTACA GGCATCGTGG TGTCACGCTC

3251 GTCGTTTGGT ATGGCTTCAT TCAGCTCCGG TTCCCAACGA TCAAGGCGAG

3301 TTACATGATC CCCCATGTTG TGCAAAAAAG CGGTTAGCTC CTTCGGTCCT

3351 CCGATCGTTG TCAGAAGTAA GTTGGCCGCA GTGTTATCAC TCATGGTTAT

3401 GGCAGCACTG CATAATTCTC TTACTGTCAT GCCATCCGTA AGATGCTTTT

3451 CTGTCACTGG TGAGTACTCA ACCAAGTCAT TCTGAGAATA GTGTATGCGG

FIG. 1b-3

```
3501 CGACCGAGTT GCTCTTGCCC GGCGTCAATA CGGGATAATA CCGCGCCACA
3551 TAGCAGAACT TTAAAAGTGC TCATCATTGG AAAACGTTCT TCGGGGCGAA
3601 AACTCTCAAG GATCTTACCG CTGTTGAGAT CCAGTTCGAT GTAACCCACT
3651 CGTGCACCCA ACTGATCTTC AGCATCTTTT ACTTTCACCA GCGTTTCTGG
3701 GTGAGCAAAA ACAGGAAGGC AAAATGCCGC AAAAAAGGGA ATAAGGGCGA
3751 CACGGAAATG TTGAATACTC ATACTCTTCC TTTTTCAATA TTATTGAAGC
3801 ATTTATCAGG GTTATTGTCT CATGAGCGGA TACATATTTG AATGTATTTA
3851 GAAAAATAAA CAAATAGGGG TTCCGCGCAC ATTTCCCCGA AAAGTGCCAC
3901 CTGACGTCTA AGAAACCATT ATTATCATGA CATTAACCTA TAAAAATAGG
3951 CGTATCACGA GGCCCTTTCG TCTTCAC
```

FIG. Ib-4

```
     HindIII
1    AAGCTTCACG CTGCCGCAAG CACTCAGGGC GCAAGGGCTG CTAAAGGAAG
51   CGGAACACGT AGAAAGCCAG TCCGCAGAAA CGGTGCTGAC CCCGGATGAA
101  TGTCAGCTAC TGGGCTATCT GGACAAGGGA AAACGCAAGC GCAAAGAGAA
151  AGCAGGTAGC TTGCAGTGGG CTTACATGGC GATAGCTAGA CTGGGCGGTT
201  TTATGGACAG CAAGCGAACC GGAATTGCCA GCTGGGGCGC CCTCTGGTAA
251  GGTTGGGAAG CCCTGCAAAG TAAACTGGAT GGCTTTCTTG CCGCCAAGGA
301  TCTGATGGCG CAGGGGATCA AGATCTGATC AAGAGACAGG ATGACGGTCG
351  TTTCGCATGC TTGAACAAGA TGGATTGCAC GCAGGTTCTC CGGCCGCTTG
401  GGTGGAGAGG CTATTCGGCT ATGACTGGGC ACAACAGACA ATCGGCTGCT
451  CTGATGCCGC CGTGTTCCGG CTGTCAGCGC AGGGGCGCCC GGTTCTTTTT
501  GTCAAGACCG ACCTGTCCGG TGCCCTGAAT GAACTGCAGG ACGAGGCAGC
551  GCGGCTATCG TGGCTGGCCA CGACGGGCGT TCCTTGCGCA GCTGTGCTCG
601  ACGTTGTCAC TGAAGCGGGA AGGGACTGGC TGCTATTGGG CGAAGTGCCG
651  GGGCAGGATC TCCTGTCATC TCACCTTGCT CCTGCCGAGA AAGTATCCAT
701  CATGGCTGAT GCAATGCGGC GGCTGCATAC GCTTGATCCG GCTACCTGCC
751  CATTCGACCA CCAAGCGAAA CATCGCATCG AGCGAGCACG TACTCGGATG
801  GAAGCCGGTC TTGTCGATCA GGATGATCTG GACGAAGAGC ATCAGGGGCT
851  CGCGCCAGCC GAACTGTTCG CCAGGCTCAA GGCGCGCATG CCCGACGGCG
901  AGGATCTCGT CGTGACCCAT GGCGATGCCT GCTTGCCGAA TATCATGGTG
951  GAAAATGGCC GCTTTTCTGG ATTCATCGAC TGTGGCCGGC TGGGTGTGGC
1001 GGACCGCTAT CAGGACATAG CGTTGGCTAC CCGTGATATT GCTGAAGAGC
1051 TTGGCGGCGA ATGGGCTGAC CGCTTCCTCG TGCTTTACGG TATCGCCGCT
1101 CCCGATTCGC AGCGCATCGC CTTCTATCGC CTTCTTGACG AGTTCTTCTG
1151 AGCGGGACTC TGGGGTTCGA AATGACCGAC CAAGCGACGC CCAACCTGCC
1201 ATCACGAGAT TTCGATTCCA CCGCCGCCTT CTATGAAAGG TTGGGCTTCG
1251 GAATCGTTTT CCGGGACGCC GGCTGGATGA TCCTCCAGCG CGGGGATCTC
1301 ATGCTGGAGT TCTTCGCCCA CCCCGGGCTC GATCCCCTCG CGAGTTGGTT
```

FIG. 2b-1

```
1351 CAGCTGCTGC CTGAGGCTGG ACGACCTCGC GGAGTTCTAC CGGCAGTGCA
1401 AATCCGTCGG CATCCAGGAA ACCAGCAGCG GCTATCCGCG CATCCATGCC
                                                SalI
1451 CCCGAACTGC AGGAGTGGGG AGGCACGATG GCCGCTTTGG TCGACAATTC
1501 GCGCTAACTT ACATTAATTG CGTTGCGCTC ACTGCCCGCT TTCCAGTCGG
1551 GAAACCTGTC GTGCCAGCTG CATTAATGAA TCGGCCAACG CGCGGGGAGA
1601 GGCGGTTTGC GTATTGGGCG CCAGGGTGGT TTTTCTTTTC ACCAGTGAGA
1651 CGGGCAACAG CTGATTGCCC TTCACCGCCT GGCCCTGAGA GAGTTGCAGC
1701 AAGCGGTCCA CGCTGGTTTG CCCCAGCAGG CGAAAATCCT GTTTGATGGT
1751 GGTTAACGGC GGGATATAAC ATGAGCTGTC TTCGGTATCG TCGTATCCCA
1801 CTACCGAGAT ATCCGCACCA ACGCGCAGCC CGGACTCGGT AATGGCGCGC
1851 ATTGCGCCCA GCGCCATCTG ATCGTTGGCA ACCAGCATCG CAGTGGGAAC
1901 GATGCCCTCA TTCAGCATTT GCATGGTTTG TTGAAAACCG GACATGGCAC
1951 TCCAGTCGCC TTCCCGTTCC GCTATCGGCT GAATTTGATT GCGAGTGAGA
2001 TATTTATGCC AGCCAGCCAG ACGCAGACGC GCCGAGACAG AACTTAATGG
2051 GCCCGCTAAC AGCGCGATTT GCTGGTGACC CAATGCGACC AGATGCTCCA
2101 CGCCCAGTCG CGTACCGTCT TCATGGGAGA AAATAATACT GTTGATGGGT
2151 GTCTGGTCAG AGACATCAAG AAATAACGCC GGAACATTAG TGCAGGCAGC
2201 TTCCACAGCA ATGGCATCCT GGTCATCCAG CGGATAGTTA ATGATCAGCC
2251 CACTGACGCG TTGCGCGAGA AGATTGTGCA CCGCCGCTTT ACAGGCTTCG
2301 ACGCCGCTTC GTTCTACCAT CGACACCACC ACGCTGGCAC CCAGTTGATC
2351 GGCGCGAGAT TTAATCGCCG CGACAATTTG CGACGGCGCG TGCAGGGCCA
2401 GACTGGAGGT GGCAACGCCA ATCAGCAACG ACTGTTTGCC CGCCAGTTGT
2451 TGTGCCACGC GGTTGGGAAT GTAATTCAGC TCCGCCATCG CCGCTTCCAC
2501 TTTTTCCCGC GTTTTCGCAG AAACGTGGCT GGCCTCCTTC ACCACGCGGG
2551 AAACGGTCTG ATAAGAGACA CCGGCATACT CTGCGACATC GTATAACGTT
2601 ACTGGTTTCA CATTCACCAC CCTGAATTGA CTCTCTTCCG GGCGCTATCA
2651 TGCCATACCG CGAAAGGTTT TGCGCCATTC GATGGTGTCA ACGTAAATGC
```

FIG.2b-2

SalI

2701 ATGCCGCTTC GCCTTCGCGC GCGAATTGTC GACCCTGTCC CTCCTGTTCA
2751 GCTACTGACG GGGTGGTGCG TAACGGCAAA AGCACCGCCG GACATCAGCG
2801 CTAGCGGAGT GTATACTGGC TTACTATGTT GGCACTGATG AGGGTGTCAG
2851 TGAAGTGCTT CATGTGGCAG GAGAAAAAAG GCTGCACCGG TGCGTCAGCA
2901 GAATATGTGA TACAGGATAT ATTCCGCTTC CTCGCTCACT GACTCGCTAC
2951 GCTCGGTCGT TCGACTGCGG CGAGCGGAAA TGGCTTACGA ACGGGGCGGA
3001 GATTTCCTGG AAGATGCCAG GAAGATACTT AACAGGGAAG TGAGAGGGCC
3051 GCGGCAAAGC CGTTTTTCCA TAGGCTCCGC CCCCCTGACA AGCATCACGA
3101 AATCTGACGC TCAAATCAGT GGTGGCGAAA CCCGACAGGA CTATAAAGAT
3151 ACCAGGCGTT TCCCCTGGCG GCTCCCTCGT GCGCTCTCCT GTTCCTGCCT
3201 TTCGGTTTAC CGGTGTCATT CCGCTGTTAT GGCCGCGTTT GTCTCATTCC
3251 ACGCCTGACA CTCAGTTCCG GGTAGGCAGT TCGCTCCAAG CTGGACTGTA
3301 TGCACAACC CCCCGTTCAG TCCGACCGCT GCGCCTTATC CGGTAACTAT
3351 CGTCTTGAGT CCAACCCGGA AAGACTGCA AAAGCACCAC TGGCAGCAGC
3401 CACTGGTAAT TGATTTAGAG GAGTTAGTCT TGAAGTCATG CGCCGGTTAA
3451 GGCTAAACTG AAAGGACAAG TTTTGGTGAC TGCGCTCCTC CAAGCCAGTT
3501 ACCTCGGTTC AAAGAGTTGG TAGCTCAGAG AACCTTCGAA AAACCGCCCT
3551 GCAAGGCGGT TTTTTCGTTT TCAGAGCAAG AGATTACGCG CAGACCAAAA
3601 CGATCTCAAG AAGATCATCT TATTAATCAG ATAAAATATT TCTAGATTTC
3651 AGTGCAATTT ATCTCTTCAA ATGTAGCACC TGAAGTCAGC CCCATACGAT
3701 ATAAGTTGTT AATTCTCATG TTTGACAGCT TATCATCGAT

FIG. 2b-3

BglI
3102 GGAAGGGCC GAGCGCAGAA GTGGTCCTGC AACTTTATCC GCCTCCATCC
3151 AGTCTATTAA TTGTTGCCGG GAAGCTAGAG TAAGTAGTTC GCCAGTTAAT
3201 AGTTTGCGCA ACGTTGTTGC CATTGCTACA GGCATCGTGG TGTCACGCTC
3251 GTCGTTTGGT ATGGCTTCAT TCAGCTCCGG TTCCCAACGA TCAAGGCGAG
3301 TTACATGATC CCCCATGTTG TGCAAAAAAG CGGTTAGCTC CTTCGGTCCT
3351 CCGATCGTTG TCAGAAGTAA GTTGGCCGCA GTGTTATCAC TCATGGTTAT
3401 GGCAGCACTG CATAATTCTC TTACTGTCAT GCCATCCGTA AGATGCTTTT
3451 CTGTGACTGG TGAGTACTCA ACCAAGTCAT TCTGAGAATA GTGTATGCGG
3501 CGACCGAGTT GCTCTTGCCC GGCGTCAATA CGGGATAATA CCGCGCCACA
3551 TAGCAGAACT TTAAAAGTGC TCATCATTGG AAAACGTTCT TCGGGGCGAA
3601 AACTCTCAAG GATCTTACCG CTGTTGAGAT CCAGTTCGAT GTAACCCACT
3651 CGTGCACCCA ACTGATCTTC AGCATCTTTT ACTTTCACCA GCGTTTCTGG
3701 GTGAGCAAAA ACAGGAAGGC AAAATGCCGC AAAAAAGGGA ATAAGGGCGA
3751 CACGGAAATG TTGAATACTC ATACTCTTCC TTTTTCAATA TTATTGAAGC
3801 ATTTATCAGG GTTATTGTCT CATGAGCGGA TACATATTTG AATGTATTTA
3851 GAAAAATAAA CAAATAGGGG TTCCGCGCAC ATTTCCCCGA AAAGTGCCAC
3901 CTGACGTCTA AGAAACCATT ATTATCATGA CATTAACCTA TAAAAATAGG
3951 CGTATCACGA GGCCCTTTCG TCTTCAC-

XhoI
1 -CTCGAGAAAT CATAAAAAAT TTATTTGCTT TGTGAGCGGA TAACAATTAT
EcoRI
51 AATAGATTCA ATTGTGAGCG GATAACAATT TCACACAGAA TTCATTAAAG
101 AGGAGAAATT AAGCATGGTC AGATCATCTT CTCGAACCCC GAGTGACAAG
Val ArgSerSerS erArgThrPr oSerAspLys
1 11
151 CCTGTAGCCC ATGTTGTAGC AAACCCTCAA GCTGAGGGGC AGCTCCAGTG
ProValAlaH isValValAl aAsnProGln AlaGluGlyG lnLeuGlnTr
21
BglI
201 GCTGAACCGC TGGGCCAATG CCCTCCTGGC
pLeuAsnArg TrpAlaAsnA laLeu
31 36

FIG. 4

```
     BglI
3102 GGAAGGGCC  GAGCGCAGAA GTGGTCCTGC AACTTTATCC GCCTCCATCC

3151 AGTCTATTAA TTGTTGCCGG GAAGCTAGAG TAAGTAGTTC GCCAGTTAAT

3201 AGTTTGCGCA ACGTTGTTGC CATTGCTACA GGCATCGTGG TGTCACGCTC

3251 GTCGTTTGGT ATGGCTTCAT TCAGCTCCGG TTCCCAACGA TCAAGGCGAG

3301 TTACATGATC CCCCATGTTG TGCAAAAAAG CGGTTAGCTC CTTCGGTCCT

3351 CCGATCGTTG TCAGAAGTAA GTTGGCCGCA GTGTTATCAC TCATGGTTAT

3401 GGCAGCACTG CATAATTCTC TTACTGTCAT GCCATCCGTA AGATGCTTTT

3451 CTGTGACTGG TGAGTACTCA ACCAAGTCAT TCTGAGAATA GTGTATGCGG

3501 CGACCGAGTT GCTCTTGCCC GGCGTCAATA CGGGATAATA CCGCGCCACA

3551 TAGCAGAACT TTAAAAGTGC TCATCATTGG AAAACGTTCT TCGGGGCGAA

3601 AACTCTCAAG GATCTTACCG CTGTTGAGAT CCAGTTCGAT GTAACCCACT

3651 CGTGCACCCA ACTGATCTTC AGCATCTTTT ACTTTCACCA GCGTTTCTGG

3701 GTGAGCAAAA ACAGGAAGGC AAAATGCCGC AAAAAAGGGA ATAAGGGCGA

3751 CACGGAAATG TTGAATACTC ATACTCTTCC TTTTTCAATA TTATTGAAGC

3801 ATTTATCAGG GTTATTGTCT CATGAGCGGA TACATATTTG AATGTATTTA

3851 GAAAAATAAA CAAATAGGGG TTCCGCGCAC ATTTCCCCGA AAAGTGCCAC

3901 CTGACGTCTA AGAAACCATT ATTATCATGA CATTAACCTA TAAAAATAGG

3951 CGTATCACGA GGCCCTTTCG TCTTCAC-

      XhoI
   1 -CTCGAGAAAT CATAAAAAAT TTATTTGCTT TGTGAGCGGA TAACAATTAT
                                                  EcoRI
  51 AATAGATTCA ATTGTGAGCG GATAACAATT TCACACAGAA TTCATTAAAG

 101 AGGAGAAATT AAGCATGGTC AGATCATCTT CTCGAACCCC GAGTGACAAG
                      Val ArgSerSerS erArgThrPr oSerAspLys
                      1                                 11
 151 CCTGTAGCCC ATGTTGTAGC AAACCCTCAA GCTGAGGGGC AGCTCCAGTG
     ProValAlaH isValValAl aAsnProGln AlaGluGlyG lnLeuGlnTr
                            BglI  21
 201 GCTGAACCGC TGGGCCAATG CCCTCCTGGC
     pSerAsnArg ArgAlaAsnA laLeu
            31               36
```

FIG. 5

```
     BglI
3102 GGAAGGGCC  GAGCGCAGAA GTGGTCCTGC AACTTTATCC GCCTCCATCC
3151 AGTCTATTAA TTGTTGCCGG GAAGCTAGAG TAAGTAGTTC GCCAGTTAAT
3201 AGTTTGCGCA ACGTTGTTGC CATTGCTACA GGCATCGTGG TGTCACGCTC
3251 GTCGTTTGGT ATGGCTTCAT TCAGCTCCGG TTCCCAACGA TCAAGGCGAG
3301 TTACATGATC CCCCATGTTG TGCAAAAAAG CGGTTAGCTC CTTCGGTCCT
3351 CCGATCGTTG TCAGAAGTAA GTTGGCCGCA GTGTTATCAC TCATGGTTAT
3401 GGCAGCACTG CATAATTCTC TTACTGTCAT GCCATCCGTA AGATGCTTTT
3451 CTGTGACTGG TGAGTACTCA ACCAAGTCAT TCTGAGAATA GTGTATGCGG
3501 CGACCGAGTT GCTCTTGCCC GGCGTCAATA CGGGATAATA CCGCGCCACA
3551 TAGCAGAACT TTAAAAGTGC TCATCATTGG AAAACGTTCT TCGGGGCGAA
3601 AACTCTCAAG GATCTTACCG CTGTTGAGAT CCAGTTCGAT GTAACCCACT
3651 CGTGCACCCA ACTGATCTTC AGCATCTTTT ACTTTCACCA GCGTTTCTGG
3701 GTGAGCAAAA ACAGGAAGGC AAAATGCCGC AAAAAAGGGA ATAAGGGCGA
3751 CACGGAAATG TTGAATACTC ATACTCTTCC TTTTTCAATA TTATTGAAGC
3801 ATTTATCAGG GTTATTGTCT CATGAGCGGA TACATATTTG AATGTATTTA
3851 GAAAAATAAA CAAATAGGGG TTCCGCGCAC ATTTCCCCGA AAAGTGCCAC
3901 CTGACGTCTA AGAAACCATT ATTATCATGA CATTAACCTA TAAAAATAGG
3951 CGTATCACGA GGCCCTTTCG TCTTCAC-

      XhoI
   1 -CTCGAGAAAT CATAAAAAAT TTATTTGCTT TGTGAGCGGA TAACAATTAT
                                                EcoRI
  51 AATAGATTCA ATTGTGAGCG GATAACAATT TCACACAGAA TTCATTAAAG

 101 AGGAGAAATT AAGCATGGTC AGATCATCTT CTCGAACCCC GAGTGACAAG
                       Val ArgSerSerS erArgThrPr oSerAspLys
                       1                                 11
 151 CCTGTAGCCC ATGTTGTAGC AAACCCTCAA GCTGAGGGGC AGCTCCAGTG
     ProValAlaH isValValAl aAsnProGln AlaGluGlyG lnLeuGlnTr
                                  21
                                BglI
 201 GCTGAACCGC TGGGCCAATG CCCTCCTGGC
     pSerAsnArg TrpAlaAsnA laLeu
              31               36
```

FIG. 6

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
( A ) LENGTH: 3977 base pairs
( B ) TYPE: nucleic acid
( C ) STRANDEDNESS: single
( D ) TOPOLOGY: circular ( i i ) MOLECULE TYPE: DNA (genomic)

( i i i ) HYPOTHETICAL: NO ( i i i ) ANTI-SENSE: NO ( v ) FRAGMENT TYPE: internal ( v i ) ORIGINAL SOURCE:
( A ) ORGANISM: Plasmid pDS56/RBSII,SphI-TNFalpha ( i x ) FEATURE:
( A ) NAME/KEY: CDS
( B ) LOCATION: 118..591

( x i ) SEQUENCE DESCRIPTION: SEQ ID NO: 1:

```
CTCGAGAAAT CATAAAAAAT TTATTTGCTT TGTGAGCGGA TAACAATTAT AATAGATTCA     60

ATTGTGAGCG GATAACAATT TCACACAGAA TTCATTAAAG AGGAGAAATT AAGCATG       117

GTC AGA TCA TCT TCT CGA ACC CCG AGT GAC AAG CCT GTA GCC CAT GTT      165
Val Arg Ser Ser Ser Arg Thr Pro Ser Asp Lys Pro Val Ala His Val
 1               5                  10                  15

GTC GCG AAC CCT CAA GCT GAG GGG CAG CTC CAG TGG CTG AAC CGC CGG      213
Val Ala Asn Pro Gln Ala Glu Gly Gln Leu Gln Trp Leu Asn Arg Arg
            20                  25                  30

GCC AAT GCC CTC CTG GCC AAT GGC GTG GAG CTG AGA GAT AAC CAG CTG      261
Ala Asn Ala Leu Leu Ala Asn Gly Val Glu Leu Arg Asp Asn Gln Leu
        35                  40                  45

GTG GTG CCA TCA GAG GGC CTG TAC CTC ATC TAC TCC CAG GTC CTC TTC      309
Val Val Pro Ser Glu Gly Leu Tyr Leu Ile Tyr Ser Gln Val Leu Phe
    50                  55                  60

AAG GGC CAA GGC TGC CCC TCC ACC CAT GTG CTC CTC ACC CAC ACC ATC      357
Lys Gly Gln Gly Cys Pro Ser Thr His Val Leu Leu Thr His Thr Ile
65                  70                  75                  80

AGC CGC ATC GCC GTC TCC TAC CAG ACC AAG GTC AAC CTC CTC TCT GCC      405
Ser Arg Ile Ala Val Ser Tyr Gln Thr Lys Val Asn Leu Leu Ser Ala
                85                  90                  95

ATC AAG AGC CCC TGC CAG AGG GAG ACC CCA GAG GGG GCT GAG GCC AAG      453
Ile Lys Ser Pro Cys Gln Arg Glu Thr Pro Glu Gly Ala Glu Ala Lys
           100                 105                 110

CCC TGG TAT GAG CCC ATC TAT CTG GGA GGG GTC TTC CAG CTG GAG AAG      501
Pro Trp Tyr Glu Pro Ile Tyr Leu Gly Gly Val Phe Gln Leu Glu Lys
       115                 120                 125

GGT GAC CGA CTC AGC GCT GAG ATC AAT CGG CCC GAC TAT CTC GAC TTT      549
Gly Asp Arg Leu Ser Ala Glu Ile Asn Arg Pro Asp Tyr Leu Asp Phe
   130                 135                 140

GCC GAG TCT GGG CAG GTC TAC TTT GGG ATC ATT GCC CTG TGAGGAGGAC       598
Ala Glu Ser Gly Gln Val Tyr Phe Gly Ile Ile Ala Leu
145                 150                 155

GAACATCCAA CCTTCCCAAA CGCCTCCCCT GCCCCAATCC CTTTATTACC CCCTCCTTCA    658

GACACCCTCA ACCTCTTCTG GCTCAAAAAG AGAATTGGGG GCTTAGGGTC GGAACCCAAG    718
```

-continued

CTTGGACTCC TGTTGATAGA TCCAGTAATG ACCTCAGAAC TCCATCTGGA TTTGTTCAGA 778

ACGCTCGGTT GCCGCCGGGC GTTTTTTATT GGTGAGAATC CAAGCTAGCT TGGCGAGATT 838

TTCAGGAGCT AAGGAAGCTA AAATGGAGAA AAAAATCACT GGATATACCA CCGTTGATAT 898

ATCCCAATGG CATCGTAAAG AACATTTTGA GGCATTTCAG TCAGTTGCTC AATGTACCTA 958

TAACCAGACC GTTCAGCTGG ATATTACGGC CTTTTTAAAG ACCGTAAAGA AAAATAAGCA 1018

CAAGTTTTAT CCGGCCTTTA TTCACATTCT TGCCCGCCTG ATGAATGCTC ATCCGGAATT 1078

TCGTATGGCA ATGAAAGACG GTGAGCTGGT GATATGGGAT AGTGTTCACC CTTGTTACAC 1138

CGTTTTCCAT GAGCAAACTG AAACGTTTTC ATCGCTCTGG AGTGAATACC ACGACGATTT 1198

CCGGCAGTTT CTACACATAT ATTCGCAAGA TGTGGCGTGT TACGGTGAAA ACCTGGCCTA 1258

TTTCCCTAAA GGGTTTATTG AGAATATGTT TTTCGTCTCA GCCAATCCCT GGGTGAGTTT 1318

CACCAGTTTT GATTTAAACG TGGCCAATAT GGACAACTTC TTCGCCCCCG TTTTCACCAT 1378

GGGCAAATAT TATACGCAAG GCGACAAGGT GCTGATGCCG CTGGCGATTC AGGTTCATCA 1438

TGCCGTCTGT GATGGCTTCC ATGTCGGCAG AATGCTTAAT GAATTACAAC AGTACTGCGA 1498

TGAGTGGCAG GGCGGGGCGT AATTTTTTTA AGGCAGTTAT TGGTGCCCTT AAACGCCTGG 1558

GGTAATGACT CTCTAGCTTG AGGCATCAAA TAAAACGAAA GGCTCAGTCG AAAGACTGGG 1618

CCTTTCGTTT TATCTGTTGT TTGTCGGTGA ACGCTCTCCT GAGTAGGACA AATCCGCCGC 1678

TCTAGAGCTG CCTCGCGCGT TTCGGTGATG ACGGTGAAAA CCTCTGACAC ATGCAGCTCC 1738

CGGAGACGGT CACAGCTTGT CTGTAAGCGG ATGCCGGGAG CAGACAAGCC CGTCAGGGCG 1798

CGTCAGCGGG TGTTGGCGGG TGTCGGGGCG CAGCCATGAC CCAGTCACGT AGCGATAGCG 1858

GAGTGTATAC TGGCTTAACT ATGCGGCATC AGAGCAGATT GTACTGAGAG TGCACCATAT 1918

GCGGTGTGAA ATACCGCACA GATGCGTAAG GAGAAAATAC CGCATCAGGC GCTCTTCCGC 1978

TTCCTCGCTC ACTGACTCGC TGCGCTCGGT CTGTCGGCTG CGGCGAGCGG TATCAGCTCA 2038

CTCAAAGGCG GTAATACGGT TATCCACAGA ATCAGGGGAT AACGCAGGAA AGAACATGTG 2098

AGCAAAAGGC CAGCAAAAGG CCAGGAACCG TAAAAAGGCC GCGTTGCTGG CGTTTTTCCA 2158

TAGGCTCCGC CCCCCTGACG AGCATCACAA AAATCGACGC TCAAGTCAGA GGTGGCGAAA 2218

CCCGACAGGA CTATAAAGAT ACCAGGCGTT TCCCCCTGGA AGCTCCCTCG TGCGCTCTCC 2278

TGTTCCGACC CTGCCGCTTA CCGGATACCT GTCCGCCTTT CTCCCTTCGG GAAGCGTGGC 2338

GCTTTCTCAA TGCTCACGCT GTAGGTATCT CAGTTCGGTG TAGGTCGTTC GCTCCAAGCT 2398

GGGCTGTGTG CACGAACCCC CCGTTCAGCC CGACCGCTGC GCCTTATCCG GTAACTATCG 2458

TCTTGAGTCC AACCCGGTAA GACACGACTT ATCGCCACTG GCAGCAGCCA CTGGTAACAG 2518

GATTAGCAGA GCGAGGTATG TAGGCGGTGC TACAGAGTTC TTGAAGTGGT GGCCTAACTA 2578

CGGCTACACT AGAAGGACAG TATTTGGTAT CTGCGCTCTG CTGAAGCCAG TTACCTTCGG 2638

AAAAAGAGTT GGTAGCTCTT GATCCGGCAA ACAAACCACC GCTGGTAGCG GTGGTTTTTT 2698

TGTTTGCAAG CAGCAGATTA CGCGCAGAAA AAAAGGATCT CAAGAAGATC CTTTGATCTT 2758

TTCTACGGGG TCTGACGCTC AGTGGAACGA AAACTCACGT TAAGGGATTT TGGTCATGAG 2818

ATTATCAAAA AGGATCTTCA CCTAGATCCT TTTAAATTAA AAATGAAGTT TTAAATCAAT 2878

CTAAAGTATA TATGAGTAAA CTTGGTCTGA CAGTTACCAA TGCTTAATCA GTGAGGCACC 2938

TATCTCAGCG ATCTGTCTAT TTCGTTCATC CATAGCTGCC TGACTCCCCG TCGTGTAGAT 2998

AACTACGATA CGGGAGGGCT TACCATCTGG CCCCAGTGCT GCAATGATAC CGCGAGACCC 3058

ACGCTCACCG GCTCCAGATT TATCAGCAAT AAACCAGCCA GCCGGAAGGG CCGAGCGCAG 3118

-continued

| | | | | | | |
|---|---|---|---|---|---|---|
| AAGTGGTCCT | GCAACTTTAT | CCGCCTCCAT | CCAGTCTATT | AATTGTTGCC | GGGAAGCTAG | 3178 |
| AGTAAGTAGT | TCGCCAGTTA | ATAGTTTGCG | CAACGTTGTT | GCCATTGCTA | CAGGCATCGT | 3238 |
| GGTGTCACGC | TCGTCGTTTG | GTATGGCTTC | ATTCAGCTCC | GGTTCCCAAC | GATCAAGGCG | 3298 |
| AGTTACATGA | TCCCCCATGT | TGTGCAAAAA | AGCGGTTAGC | TCCTTCGGTC | CTCCGATCGT | 3358 |
| TGTCAGAAGT | AAGTTGGCCG | CAGTGTTATC | ACTCATGGTT | ATGGCAGCAC | TGCATAATTC | 3418 |
| TCTTACTGTC | ATGCCATCCG | TAAGATGCTT | TTCTGTGACT | GGTGAGTACT | CAACCAAGTC | 3478 |
| ATTCTGAGAA | TAGTGTATGC | GGCGACCGAG | TTGCTCTTGC | CCGGCGTCAA | TACGGGATAA | 3538 |
| TACCGCGCCA | CATAGCAGAA | CTTTAAAAGT | GCTCATCATT | GGAAAACGTT | CTTCGGGGCG | 3598 |
| AAAACTCTCA | AGGATCTTAC | CGCTGTTGAG | ATCCAGTTCG | ATGTAACCCA | CTCGTGCACC | 3658 |
| CAACTGATCT | TCAGCATCTT | TTACTTTCAC | CAGCGTTTCT | GGGTGAGCAA | AAACAGGAAG | 3718 |
| GCAAAATGCC | GCAAAAAAGG | GAATAAGGGC | GACACGGAAA | TGTTGAATAC | TCATACTCTT | 3778 |
| CCTTTTTCAA | TATTATTGAA | GCATTTATCA | GGGTTATTGT | CTCATGAGCG | GATACATATT | 3838 |
| TGAATGTATT | TAGAAAAATA | AACAAATAGG | GGTTCCGCGC | ACATTTCCCC | GAAAAGTGCC | 3898 |
| ACCTGACGTC | TAAGAAACCA | TTATTATCAT | GACATTAACC | TATAAAAATA | GGCGTATCAC | 3958 |
| GAGGCCCTTT | CGTCTTCAC | | | | | 3977 |

( 2 ) INFORMATION FOR SEQ ID NO: 2:

( i ) SEQUENCE CHARACTERISTICS:
( A ) LENGTH: 157 amino acids
( B ) TYPE: amino acid
( D ) TOPOLOGY: linear ( i i ) MOLECULE TYPE: protein ( x i ) SEQUENCE DESCRIPTION: SEQ ID NO: 2:

```
Val Arg Ser Ser Ser Arg Thr Pro Ser Asp Lys Pro Val Ala His Val
  1               5                  10                  15

Val Ala Asn Pro Gln Ala Glu Gly Gln Leu Gln Trp Leu Asn Arg Arg
             20                  25                  30

Ala Asn Ala Leu Leu Ala Asn Gly Val Glu Leu Arg Asp Asn Gln Leu
         35                  40                  45

Val Val Pro Ser Glu Gly Leu Tyr Leu Ile Tyr Ser Gln Val Leu Phe
     50                  55                  60

Lys Gly Gln Gly Cys Pro Ser Thr His Val Leu Leu Thr His Thr Ile
 65                  70                  75                  80

Ser Arg Ile Ala Val Ser Tyr Gln Thr Lys Val Asn Leu Leu Ser Ala
                 85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

( 2 ) INFORMATION FOR SEQ ID NO: 3:

( i ) SEQUENCE CHARACTERISTICS:
( A ) LENGTH: 3740 base pairs
( B ) TYPE: nucleic acid
( C ) STRANDEDNESS: single ( D ) TOPOLOGY: circular ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Plasmid pREP4

( x i ) SEQUENCE DESCRIPTION: SEQ ID NO: 3:

| | | | | | | |
|---|---|---|---|---|---|---|
| AAGCTTCACG | CTGCCGCAAG | CACTCAGGGC | GCAAGGGCTG | CTAAAGGAAG | CGGAACACGT | 60 |
| AGAAAGCCAG | TCCGCAGAAA | CGGTGCTGAC | CCCGGATGAA | TGTCAGCTAC | TGGGCTATCT | 120 |
| GGACAAGGGA | AAACGCAAGC | GCAAAGAGAA | AGCAGGTAGC | TTGCAGTGGG | CTTACATGGC | 180 |
| GATAGCTAGA | CTGGGCGGTT | TTATGGACAG | CAAGCGAACC | GGAATTGCCA | GCTGGGGCGC | 240 |
| CCTCTGGTAA | GGTTGGGAAG | CCCTGCAAAG | TAAACTGGAT | GGCTTTCTTG | CCGCCAAGGA | 300 |
| TCTGATGGCG | CAGGGGATCA | AGATCTGATC | AAGAGACAGG | ATGACGGTCG | TTTCGCATGC | 360 |
| TTGAACAAGA | TGGATTGCAC | GCAGGTTCTC | CGGCCGCTTG | GGTGGAGAGG | CTATTCGGCT | 420 |
| ATGACTGGGC | ACAACAGACA | ATCGGCTGCT | CTGATGCCGC | CGTGTTCCGG | CTGTCAGCGC | 480 |
| AGGGGCGCCC | GGTTCTTTTT | GTCAAGACCG | ACCTGTCCGG | TGCCCTGAAT | GAACTGCAGG | 540 |
| ACGAGGCAGC | GCGGCTATCG | TGGCTGGCCA | CGACGGGCGT | TCCTTGCGCA | GCTGTGCTCG | 600 |
| ACGTTGTCAC | TGAAGCGGGA | AGGGACTGGC | TGCTATTGGG | CGAAGTGCCG | GGGCAGGATC | 660 |
| TCCTGTCATC | TCACCTTGCT | CCTGCCGAGA | AAGTATCCAT | CATGGCTGAT | GCAATGCGGC | 720 |
| GGCTGCATAC | GCTTGATCCG | GCTACCTGCC | CATTCGACCA | CCAAGCGAAA | CATCGCATCG | 780 |
| AGCGAGCACG | TACTCGGATG | GAAGCCGGTC | TTGTCGATCA | GGATGATCTG | GACGAAGAGC | 840 |
| ATCAGGGGCT | CGCGCCAGCC | GAACTGTTCG | CCAGGCTCAA | GGCGCGCATG | CCCGACGGCG | 900 |
| AGGATCTCGT | CGTGACCCAT | GGCGATGCCT | GCTTGCCGAA | TATCATGGTG | GAAAATGGCC | 960 |
| GCTTTTCTGG | ATTCATCGAC | TGTGGCCGGC | TGGGTGTGGC | GGACCGCTAT | CAGGACATAG | 1020 |
| CGTTGGCTAC | CCGTGATATT | GCTGAAGAGC | TTGGCGGCGA | ATGGGCTGAC | CGCTTCCTCG | 1080 |
| TGCTTTACGG | TATCGCCGCT | CCCGATTCGC | AGCGCATCGC | CTTCTATCGC | CTTCTTGACG | 1140 |
| AGTTCTTCTG | AGCGGGACTC | TGGGGTTCGA | AATGACCGAC | CAAGCGACGC | CCAACCTGCC | 1200 |
| ATCACGAGAT | TTCGATTCCA | CCGCCGCCTT | CTATGAAAGG | TTGGGCTTCG | GAATCGTTTT | 1260 |
| CCGGGACGCC | GGCTGGATGA | TCCTCCAGCG | CGGGGATCTC | ATGCTGGAGT | TCTTCGCCCA | 1320 |
| CCCCGGGCTC | GATCCCCTCG | CGAGTTGGTT | CAGCTGCTGC | CTGAGGCTGG | ACGACCTCGC | 1380 |
| GGAGTTCTAC | CGGCAGTGCA | AATCCGTCGG | CATCCAGGAA | ACCAGCAGCG | GCTATCCGCG | 1440 |
| CATCCATGCC | CCCGAACTGC | AGGAGTGGGG | AGGCACGATG | GCCGCTTTGG | TCGACAATTC | 1500 |
| GCGCTAACTT | ACATTAATTG | CGTTGCGCTC | ACTGCCCGCT | TTCCAGTCGG | GAAACCTGTC | 1560 |
| GTGCCAGCTG | CATTAATGAA | TCGGCCAACG | CGCGGGGAGA | GGCGGTTTGC | GTATTGGGCG | 1620 |
| CCAGGGTGGT | TTTTCTTTTC | ACCAGTGAGA | CGGGCAACAG | CTGATTGCCC | TTCACCGCCT | 1680 |
| GGCCCTGAGA | GAGTTGCAGC | AAGCGGTCCA | CGCTGGTTTG | CCCCAGCAGG | CGAAAATCCT | 1740 |
| GTTTGATGGT | GGTTAACGGC | GGGATATAAC | ATGAGCTGTC | TTCGGTATCG | TCGTATCCCA | 1800 |
| CTACCGAGAT | ATCCGCACCA | ACGCGCAGCC | CGGACTCGGT | AATGGCGCGC | ATTGCGCCCA | 1860 |
| GCGCCATCTG | ATCGTTGGCA | ACCAGCATCG | CAGTGGGAAC | GATGCCCTCA | TTCAGCATTT | 1920 |
| GCATGGTTTG | TTGAAAACCG | GACATGGCAC | TCCAGTCGCC | TTCCCGTTCC | GCTATCGGCT | 1980 |
| GAATTTGATT | GCGAGTGAGA | TATTTATGCC | AGCCAGCCAG | ACGCAGACGC | GCCGAGACAG | 2040 |

-continued

| | | | | | | |
|---|---|---|---|---|---|---|
| AACTTAATGG | GCCCGCTAAC | AGCGCGATTT | GCTGGTGACC | CAATGCGACC | AGATGCTCCA | 2100 |
| CGCCCAGTCG | CGTACCGTCT | TCATGGGAGA | AAATAATACT | GTTGATGGGT | GTCTGGTCAG | 2160 |
| AGACATCAAG | AAATAACGCC | GGAACATTAG | TGCAGGCAGC | TTCCACAGCA | ATGGCATCCT | 2220 |
| GGTCATCCAG | CGGATAGTTA | ATGATCAGCC | CACTGACGCG | TTGCGCGAGA | AGATTGTGCA | 2280 |
| CCGCCGCTTT | ACAGGCTTCG | ACGCCGCTTC | GTTCTACCAT | CGACACCACC | ACGCTGGCAC | 2340 |
| CCAGTTGATC | GGCGCGAGAT | TTAATCGCCG | CGACAATTTG | CGACGGCGCG | TGCAGGGCCA | 2400 |
| GACTGGAGGT | GGCAACGCCA | ATCAGCAACG | ACTGTTTGCC | CGCCAGTTGT | TGTGCCACGC | 2460 |
| GGTTGGGAAT | GTAATTCAGC | TCCGCCATCG | CCGCTTCCAC | TTTTTCCCGC | GTTTTCGCAG | 2520 |
| AAACGTGGCT | GGCCTGGTTC | ACCACGCGGG | AAACGGTCTG | ATAAGAGACA | CCGGCATACT | 2580 |
| CTGCGACATC | GTATAACGTT | ACTGGTTTCA | CATTCACCAC | CCTGAATTGA | CTCTCTTCCG | 2640 |
| GGCGCTATCA | TGCCATACCG | CGAAAGGTTT | TGCGCCATTC | GATGGTGTCA | ACGTAAATGC | 2700 |
| ATGCCGCTTC | GCCTTCGCGC | GCGAATTGTC | GACCCTGTCC | CTCCTGTTCA | GCTACTGACG | 2760 |
| GGGTGGTGCG | TAACGGCAAA | AGCACCGCCG | GACATCAGCG | CTAGCGGAGT | GTATACTGGC | 2820 |
| TTACTATGTT | GGCACTGATG | AGGGTGTCAG | TGAAGTGCTT | CATGTGGCAG | GAGAAAAAAG | 2880 |
| GCTGCACCGG | TGCGTCAGCA | GAATATGTGA | TACAGGATAT | ATTCCGCTTC | CTCGCTCACT | 2940 |
| GACTCGCTAC | GCTCGGTCGT | TCGACTGCGG | CGAGCGGAAA | TGGCTTACGA | ACGGGGCGGA | 3000 |
| GATTTCCTGG | AAGATGCCAG | GAAGATACTT | AACAGGGAAG | TGAGAGGGCC | GCGGCAAAGC | 3060 |
| CGTTTTTCCA | TAGGCTCCGC | CCCCCTGACA | AGCATCACGA | AATCTGACGC | TCAAATCAGT | 3120 |
| GGTGGCGAAA | CCCGACAGGA | CTATAAAGAT | ACCAGGCGTT | TCCCCTGGCG | GCTCCCTCGT | 3180 |
| GCGCTCTCCT | GTTCCTGCCT | TTCGGTTTAC | CGGTGTCATT | CCGCTGTTAT | GGCCGCGTTT | 3240 |
| GTCTCATTCC | ACGCCTGACA | CTCAGTTCCG | GGTAGGCAGT | TCGCTCCAAG | CTGGACTGTA | 3300 |
| TGCACGAACC | CCCCGTTCAG | TCCGACCGCT | GCGCCTTATC | CGGTAACTAT | CGTCTTGAGT | 3360 |
| CCAACCCGGA | AAGACATGCA | AAAGCACCAC | TGGCAGCAGC | CACTGGTAAT | TGATTTAGAG | 3420 |
| GAGTTAGTCT | TGAAGTCATG | CGCCGGTTAA | GGCTAAACTG | AAAGGACAAG | TTTTGGTGAC | 3480 |
| TGCGCTCCTC | CAAGCCAGTT | ACCTCGGTTC | AAAGAGTTGG | TAGCTCAGAG | AACCTTCGAA | 3540 |
| AAACCGCCCT | GCAAGGCGGT | TTTTTCGTTT | TCAGAGCAAG | AGATTACGCG | CAGACCAAAA | 3600 |
| CGATCTCAAG | AAGATCATCT | TATTAATCAG | ATAAAATATT | TCTAGATTTC | AGTGCAATTT | 3660 |
| ATCTCTTCAA | ATGTAGCACC | TGAAGTCAGC | CCCATACGAT | ATAAGTTGTT | AATTCTCATG | 3720 |
| TTTGACAGCT | TATCATCGAT | | | | | 3740 |

( 2 ) INFORMATION FOR SEQ ID NO: 4:

( i ) SEQUENCE CHARACTERISTICS:
( A ) LENGTH: 1106 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v ) FRAGMENT TYPE: N-terminal ( v i ) ORIGINAL SOURCE:
( A ) ORGANISM: Plasmid pDS56/RBSII,SphI-THFalpha(Trp32)

( i x ) FEATURE:

( A ) NAME/KEY: CDS
( B ) LOCATION: 994..1104

( x i ) SEQUENCE DESCRIPTION: SEQ ID NO: 4:

```
GGAAGGGCCG AGCGCAGAAG TGGTCCTGCA ACTTTATCCG CCTCCATCCA GTCTATTAAT     60
TGTTGCCGGG AAGCTAGAGT AAGTAGTTCG CCAGTTAATA GTTTGCGCAA CGTTGTTGCC    120
ATTGCTACAG GCATCGTGGT GTCACGCTCG TCGTTTGGTA TGGCTTCATT CAGCTCCGGT    180
TCCCAACGAT CAAGGCGAGT TACATGATCC CCCATGTTGT GCAAAAAAGC GGTTAGCTCC    240
TTCGGTCCTC CGATCGTTGT CAGAAGTAAG TTGGCCGCAG TGTTATCACT CATGGTTATG    300
GCAGCACTGC ATAATTCTCT TACTGTCATG CCATCCGTAA GATGCTTTTC TGTGACTGGT    360
GAGTACTCAA CCAAGTCATT CTGAGAATAG TGTATGCGGC GACCGAGTTG CTCTTGCCCG    420
GCGTCAATAC GGGATAATAC CGCGCCACAT AGCAGAACTT TAAAAGTGCT CATCATTGGA    480
AAACGTTCTT CGGGGCGAAA ACTCTCAAGG ATCTTACCGC TGTTGAGATC CAGTTCGATG    540
TAACCCACTC GTGCACCCAA CTGATCTTCA GCATCTTTTA CTTTCACCAG CGTTTCTGGG    600
TGAGCAAAAA CAGGAAGGCA AAATGCCGCA AAAAAGGGAA TAAGGGCGAC ACGGAAATGT    660
TGAATACTCA TACTCTTCCT TTTTCAATAT TATTGAAGCA TTTATCAGGG TTATTGTCTC    720
ATGAGCGGAT ACATATTTGA ATGTATTTAG AAAAATAAAC AAATAGGGGT TCCGCGCACA    780
TTTCCCCGAA AAGTGCCACC TGACGTCTAA GAAACCATTA TTATCATGAC ATTAACCTAT    840
AAAAATAGGC GTATCACGAG GCCCTTTCGT CTTCACCTCG AGAAATCATA AAAAATTTAT    900
TTGCTTTGTG AGCGGATAAC AATTATAATA GATTCAATTG TGAGCGGATA ACAATTTCAC    960
ACAGAATTCA TTAAAGAGGA GAAATTAAGC ATG GTC AGA TCA TCT TCT CGA ACC     1014
                                     Val Arg Ser Ser Ser Arg Thr
                                      1               5

CCG AGT GAC AAG CCT GTA GCC CAT GTT GTA GCA AAC CCT CAA GCT GAG     1062
Pro Ser Asp Lys Pro Val Ala His Val Val Ala Asn Pro Gln Ala Glu
         10                  15                  20

GGG CAG CTC CAG TGG CTG AAC CGC TGG GCC AAT GCC CTC CTG             1104
Gly Gln Leu Gln Trp Leu Asn Arg Trp Ala Asn Ala Leu Leu
     25                  30                  35

GC                                                                  1106
```

( 2 ) INFORMATION FOR SEQ ID NO: 5:

( i ) SEQUENCE CHARACTERISTICS:
( A ) LENGTH: 37 amino acids
( B ) TYPE: amino acid
( D ) TOPOLOGY: linear ( i i ) MOLECULE TYPE: protein ( x i ) SEQUENCE DESCRIPTION: SEQ ID NO: 5:

```
Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Trp
             20                  25                  30

Ala Asn Ala Leu Leu
         35
```

( 2 ) INFORMATION FOR SEQ ID NO: 6:

( i ) SEQUENCE CHARACTERISTICS:
( A ) LENGTH: 1106 base pairs
( B ) TYPE: nucleic acid
( C ) STRANDEDNESS: single
( D ) TOPOLOGY: linear -continued ( i i ) MOLECULE TYPE: DNA (genomic)

( i i i ) HYPOTHETICAL: NO ( i i i ) ANTI-SENSE: NO ( v ) FRAGMENT TYPE: N-terminal ( v i ) ORIGINAL SOURCE:
( A ) ORGANISM: Plasmid pDS56/RBSII,SphI-TNFalpha(Ser29)

( i x ) FEATURE:
( A ) NAME/KEY: CDS
( B ) LOCATION: 994..1104

( x i ) SEQUENCE DESCRIPTION: SEQ ID NO: 6:

```
GGAAGGGCCG AGCGCAGAAG TGGTCCTGCA ACTTTATCCG CCTCCATCCA GTCTATTAAT      60

TGTTGCCGGG AAGCTAGAGT AAGTAGTTCG CCAGTTAATA GTTTGCGCAA CGTTGTTGCC     120

ATTGCTACAG GCATCGTGGT GTCACGCTCG TCGTTTGGTA TGGCTTCATT CAGCTCCGGT     180

TCCCAACGAT CAAGGCGAGT TACATGATCC CCCATGTTGT GCAAAAAAGC GGTTAGCTCC     240

TTCGGTCCTC CGATCGTTGT CAGAAGTAAG TTGGCCGCAG TGTTATCACT CATGGTTATG     300

GCAGCACTGC ATAATTCTCT TACTGTCATG CCATCCGTAA GATGCTTTTC TGTGACTGGT     360

GAGTACTCAA CCAAGTCATT CTGAGAATAG TGTATGCGGC GACCGAGTTG CTCTTGCCCG     420

GCGTCAATAC GGGATAATAC CGCGCCACAT AGCAGAACTT TAAAAGTGCT CATCATTGGA     480

AAACGTTCTT CGGGGCGAAA ACTCTCAAGG ATCTTACCGC TGTTGAGATC CAGTTCGATG     540

TAACCCACTC GTGCACCCAA CTGATCTTCA GCATCTTTTA CTTTCACCAG CGTTTCTGGG     600

TGAGCAAAAA CAGGAAGGCA AAATGCCGCA AAAAAGGGAA TAAGGGCGAC ACGGAAATGT     660

TGAATACTCA TACTCTTCCT TTTTCAATAT TATTGAAGCA TTTATCAGGG TTATTGTCTC     720

ATGAGCGGAT ACATATTTGA ATGTATTTAG AAAAATAAAC AAATAGGGGT TCCGCGCACA     780

TTTCCCCGAA AAGTGCCACC TGACGTCTAA GAAACCATTA TTATCATGAC ATTAACCTAT     840

AAAAATAGGC GTATCACGAG GCCCTTTCGT CTTCACCTCG AGAAATCATA AAAAATTTAT     900

TTGCTTTGTG AGCGGATAAC AATTATAATA GATTCAATTG TGAGCGGATA ACAATTTCAC     960

ACAGAATTCA TTAAAGAGGA GAAATTAAGC ATG GTC AGA TCA TCT TCT CGA ACC     1014
                                     Val Arg Ser Ser Ser Arg Thr
                                      1               5

CCG AGT GAC AAG CCT GTA GCC CAT GTT GTA GCA AAC CCT CAA GCT GAG     1062
Pro Ser Asp Lys Pro Val Ala His Val Val Ala Asn Pro Gln Ala Glu
         10                  15                  20

GGG CAG CTC CAG TGG TCC AAC CGC CGG GCC AAT GCC CTC CTG             1104
Gly Gln Leu Gln Trp Ser Asn Arg Arg Ala Asn Ala Leu Leu
     25                  30                  35

GC                                                                  1106
```

( 2 ) INFORMATION FOR SEQ ID NO: 7:

( i ) SEQUENCE CHARACTERISTICS:
( A ) LENGTH: 37 amino acids
( B ) TYPE: amino acid
( D ) TOPOLOGY: linear ( i i ) MOLECULE TYPE: protein ( x i ) SEQUENCE DESCRIPTION: SEQ ID NO: 7:

```
Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Ser Asn Arg Arg
```

-continued 20 25 30

Ala Asn Ala Leu Leu
35

(2) INFORMATION FOR SEQ ID NO: 8:

(i) SEQUENCE CHARACTERISTICS:
(A) LENGTH: 1106 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
(A) ORGANISM: Plasmid pDS56/RBSII,SphI-TNFalpha(Ser29Trp32)

(ix) FEATURE:
(A) NAME/KEY: CDS
(B) LOCATION: 994..1104

(xi) SEQUENCE DESCRIPTION: SEQ ID NO: 8:

GGAAGGGCCG AGCGCAGAAG TGGTCCTGCA ACTTTATCCG CCTCCATCCA GTCTATTAAT 60

TGTTGCCGGG AAGCTAGAGT AAGTAGTTCG CCAGTTAATA GTTTGCGCAA CGTTGTTGCC 120

ATTGCTACAG GCATCGTGGT GTCACGCTCG TCGTTTGGTA TGGCTTCATT CAGCTCCGGT 180

TCCCAACGAT CAAGGCGAGT TACATGATCC CCCATGTTGT GCAAAAAAGC GGTTAGCTCC 240

TTCGGTCCTC CGATCGTTGT CAGAAGTAAG TTGGCCGCAG TGTTATCACT CATGGTTATG 300

GCAGCACTGC ATAATTCTCT TACTGTCATG CCATCCGTAA GATGCTTTTC TGTGACTGGT 360

GAGTACTCAA CCAAGTCATT CTGAGAATAG TGTATGCGGC GACCGAGTTG CTCTTGCCCG 420

GCGTCAATAC GGGATAATAC CGCGCCACAT AGCAGAACTT TAAAAGTGCT CATCATTGGA 480

AAACGTTCTT CGGGGCGAAA ACTCTCAAGG ATCTTACCGC TGTTGAGATC CAGTTCGATG 540

TAACCCACTC GTGCACCCAA CTGATCTTCA GCATCTTTTA CTTTCACCAG CGTTTCTGGG 600

TGAGCAAAAA CAGGAAGGCA AAATGCCGCA AAAAAGGGAA TAAGGGCGAC ACGGAAATGT 660

TGAATACTCA TACTCTTCCT TTTTCAATAT TATTGAAGCA TTTATCAGGG TTATTGTCTC 720

ATGAGCGGAT ACATATTTGA ATGTATTTAG AAAAATAAAC AAATAGGGGT TCCGCGCACA 780

TTTCCCCGAA AAGTGCCACC TGACGTCTAA GAAACCATTA TTATCATGAC ATTAACCTAT 840

AAAAATAGGC GTATCACGAG GCCCTTTCGT CTTCACCTCG AGAAATCATA AAAAATTTAT 900

TTGCTTTGTG AGCGGATAAC AATTATAATA GATTCAATTG TGAGCGGATA ACAATTTCAC 960

ACAGAATTCA TTAAAGAGGA GAAATTAAGC ATG GTC AGA TCA TCT TCT CGA ACC 1014
Val Arg Ser Ser Ser Arg Thr
1 5

CCG AGT GAC AAG CCT GTA GCC CAT GTT GTA GCA AAC CCT CAA GCT GAG 1062
Pro Ser Asp Lys Pro Val Ala His Val Val Ala Asn Pro Gln Ala Glu
10 15 20

GGG CAG CTC CAG TGG TCC AAC CGC TGG GCC AAT GCC CTC CTG 1104
Gly Gln Leu Gln Trp Ser Asn Arg Trp Ala Asn Ala Leu Leu
25 30 35

GC 1106

(2) INFORMATION FOR SEQ ID NO: 9:

-continued ( i ) SEQUENCE CHARACTERISTICS:
( A ) LENGTH: 37 amino acids
( B ) TYPE: amino acid
( D ) TOPOLOGY: linear ( i i ) MOLECULE TYPE: protein ( x i ) SEQUENCE DESCRIPTION: SEQ ID NO: 9:

Val Arg Ser Ser Ser Arg Thr Pro Ser Asp Lys Pro Val Ala His Val
1 5 10 15

Val Ala Asn Pro Gln Ala Glu Gly Gln Leu Gln Trp Ser Asn Arg Trp
20 25 30

Ala Asn Ala Leu Leu
35

( 2 ) INFORMATION FOR SEQ ID NO: 10:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Primer 17/F ( x i ) SEQUENCE DESCRIPTION: SEQ ID NO: 10:

GGCGTATCAC GAGGCCCTTT CG 22

( 2 ) INFORMATION FOR SEQ ID NO: 11:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Primer 17/0

( x i ) SEQUENCE DESCRIPTION: SEQ ID NO: 11:

CATTACTGGA TCTATCAACA GG 22

( 2 ) INFORMATION FOR SEQ ID NO: 12:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Primer 21/M5

-continued ( x i ) SEQUENCE DESCRIPTION: SEQ ID NO: 12:

ATTGGCCCGC TCGTTCAGCC ACTGGAGCTG CCCCTC 36

( 2 ) INFORMATION FOR SEQ ID NO: 13:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Primer 21/M6

( x i ) SEQUENCE DESCRIPTION: SEQ ID NO: 13:

ATTGGCAGTG TTGTTCAGCC ACTGGAGCTG CCCCTC 36

( 2 ) INFORMATION FOR SEQ ID NO: 14:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Primer 21/MR ( x i ) SEQUENCE DESCRIPTION: SEQ ID NO: 14:

GCCCTCCTGG CCAATGGCGT GG 22

( 2 ) INFORMATION FOR SEQ ID NO: 15:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Primer 29/M22

( x i ) SEQUENCE DESCRIPTION: SEQ ID NO: 15:

GTAGGTGACG GCGATGCGGC TGATGGT 27

( 2 ) INFORMATION FOR SEQ ID NO: 16:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

-continued ( i i i ) HYPOTHETICAL: NO ( i i i ) ANTI-SENSE: NO ( v i ) ORIGINAL SOURCE:
( A ) ORGANISM: Primer 29/MR1

( x i ) SEQUENCE DESCRIPTION: SEQ ID NO: 16:

CAGACCAAGG TCAACCTCCT C 21

( 2 ) INFORMATION FOR SEQ ID NO: 17:

( i ) SEQUENCE CHARACTERISTICS:
( A ) LENGTH: 157 amino acids
( B ) TYPE: amino acid
( D ) TOPOLOGY: linear ( i i ) MOLECULE TYPE: protein ( x i ) SEQUENCE DESCRIPTION: SEQ ID NO: 17:

| | | | | | | | | | | | | | | | |
|---|---|---|---|---|---|---|---|---|---|---|---|---|---|---|---|
| Val | Arg | Ser | Ser | Ser | Arg | Thr | Pro | Ser | Asp | Lys | Pro | Val | Ala | His | Val |
| 1 | | | | 5 | | | | | 10 | | | | | 15 | |
| Val | Ala | Asn | Pro | Gln | Ala | Glu | Gly | Gln | Leu | Gln | Trp | Xaa | Asn | Xaa | Xaa |
| | | | 20 | | | | | 25 | | | | | 30 | | |
| Ala | Asn | Ala | Leu | Leu | Ala | Asn | Gly | Val | Glu | Leu | Arg | Asp | Asn | Gln | Leu |
| | | 35 | | | | | 40 | | | | | 45 | | | |
| Val | Val | Pro | Ser | Glu | Gly | Leu | Tyr | Leu | Ile | Tyr | Ser | Gln | Val | Leu | Phe |
| | 50 | | | | | 55 | | | | | 60 | | | | |
| Lys | Gly | Gln | Gly | Cys | Pro | Ser | Thr | His | Val | Leu | Leu | Thr | His | Thr | Ile |
| 65 | | | | | 70 | | | | | 75 | | | | | 80 |
| Ser | Arg | Ile | Ala | Val | Ser | Tyr | Gln | Thr | Lys | Val | Asn | Leu | Leu | Ser | Ala |
| | | | | 85 | | | | | 90 | | | | | 95 | |
| Ile | Lys | Ser | Pro | Cys | Gln | Arg | Glu | Thr | Pro | Glu | Gly | Ala | Glu | Ala | Lys |
| | | | 100 | | | | | 105 | | | | | 110 | | |
| Pro | Trp | Tyr | Glu | Pro | Ile | Tyr | Leu | Gly | Gly | Val | Phe | Gln | Leu | Glu | Lys |
| | | 115 | | | | | 120 | | | | | 125 | | | |
| Gly | Asp | Arg | Leu | Ser | Ala | Glu | Ile | Asn | Arg | Pro | Asp | Tyr | Leu | Asp | Phe |
| | 130 | | | | | 135 | | | | | 140 | | | | |
| Ala | Glu | Ser | Gly | Gln | Val | Tyr | Phe | Gly | Ile | Ile | Ala | Leu | | | |
| 145 | | | | | 150 | | | | | 155 | | | | | |

TNF-MUTEINS

BACKGROUND OF THE INVENTION

Tumor Necrosis Factor, or more specifically Tumor Necrosis Factor-alpha (TNF-α), is a cytokine, primarily produced by stimulated macrophages, that exhibits not only a striking cytotoxicity against various rumour cells [Carswell et al., Proc. Nat. Acad. Sci., U.S.A. 72, 3666–3670, (1975)] but also plays a multiple role as a mediator of inflammation and the immune response [for an overview see Beutler and Cerami, Ann. Rev. Immunol. 7, 625–655 (1989); Bonavista and Granger (eds.) "Tumor Necrosis Factor: Structure, Mechanism of Action, Role in Disease and Therapy, Karger, Basel (1990)]. The primary structure of human Tumor Necrosis Factor-alpha (hTNF-α) has been deduced from the nucleotide sequence of a eDNA which has been cloned and expressed in *E. coli* [Pennica et al., Nature 312, 724–729 (1984); Marmenout et al., Eur. J. Biochem. 152, 515–522 (1985); Wang et al., Science 228, 149–154 (1985); Shirai et al., Nature 313, 803–806 (1985)]. A striking homology in amino acid sequence (30%) was found between hTNF-α and human Lymphotoxin, often referred to as human Tumor Necrosis Factor-beta (hTNF-β), a cytokine mainly produced by lymphocytes [Gray et al., Nature 312, 721–724 (1984); Fiers et al., Cold Spring Harbour Symp. 51, 587–595 (1986)].

h TNF-α with modified amino acid sequences, so called TNF-α-muteins, have also been described in the art [for example see Yamagishi et al., Protein Engineering 3, 713–719, (1990) or Fiers in "Tumor Necrosis Factors: Structure, Function and Mechanism of Action", Aggarwal and Vilcek (eds.), Marcel Dekker, Inc., New York, in press, or Fiers et al. in Bonavista and Granger, pp. 77–81 (s.a.)]. In addition TNF-α-muteins have also been the object of several patent applications, e.g. International Patent Applications Publ. Nos. WO 86/02381, WO 86/04606, WO 88/06625 and European Patent Applications Publ. Nos. 155,549; 158,286; 168,214; 251,037 and 340,333, and Deutsche Offenlegungsschrift Nr. 3843534.

Muteins of Lymphotoxin have also been disclosed in the art, e.g. in European Patent Applications Publ. Nos. 250,000; 314,094 and 336,383.

The biological effects of TNF are mediated via specific receptors, namely a receptor with an apparent molecular weight of 55 kD on sodium dodecylsulfate polyacrylamide gel electrophoresis (SDS-PAGE) (p55-TNF-R) and a receptor with an apparent molecular weight of 75 kD on SDS-PAGE (p75-TNF-R). Both forms of TNF-receptor have been cloned, p55-TNF-R by Loetscher et al. [Cell 61, 351–359, (1990)] and p75-TNF-R by Dembic et al. [Cytokine 2, 53–58, (1990)] (for both receptors see also European Patent Application No. 90116707.2). It was recently found that both receptors bind not only TNF-α but also TNF-β with high affinity [Schönfeld et al., J. Biol. Chem. 266, 3863–3869 (1991)].

It is well known in the art that on the basis of its biological activities TNF-α can be a valuable compound for the treatment of various disorders. For example TNF-α, alone or in combination with interferon, can be an effective antitumor agent [Brouckaert et al., Int. J. Cancer 38, 763–769 (1986)]. However, its systemic toxicity is a limit to its wider therapeutic use [Taguchi T. and Sohmura Y., Biotherapy 3, 177–186 (1991)].

It has been shown that human TNF-α (hTNF-α) in mice only binds to the 55 kD mouse TNF receptor (murine p55-TNF-R) and is far less toxic than murine TNF-α (mTNF-α), which binds to both p55-TNF-R and p75-TNF-R. In C57B16 mice, the LD50 of mTNFα is about 10 μg/mouse and the LD50 of hTNF-α is about 500 μg/mouse [Brouckaert et al., Agents and Actions 26, 196–198 (1989); Everaerdt, B. et al., Biochem. Biophys. Res. Comm. 163, 378–385 (1989); Lewis, M. et al., Proc. Natl. Acad. Sci. USA 88, 2830 (1991)]. Hence the p75-TNF-R seems to play a special role in systemic toxicity.

hTNF-α and mTNF-α bind almost equally well to human p55-TNF-R (hp55-TNF-R) and to human p75-TNF-R (hp75-TNF-R). However, hTNF-α mutants, which have retained the biological activity mediated by hp55-TNF-R but have lost nearly all activity mediated by hp75-TNF-R, are the functional equivalent of hTNF-α in the murine system in that they are expected to have reduced systemic toxicity in primates just as hTNF-α. has reduced toxicity in mice and fails to bind mouse p75-TNF-R.

Human Tumor Necrosis Factor muteins showing a significant difference between their binding affinity to the human p75-Tumor-Necrosis-Factor-Receptor (hp75-TNF-R) and to the human p55-Tumor-Necrosis-Factor-Receptor (hp55-TNF-R), have been described in European Patent No. 486 908.

SUMMARY OF THE INVENTION

This invention is directed to hTNF muteins or pharmaceutically acceptable salts thereof having the amino acid sequence of human Tumor Necrosis Factor but substituted at least at position 86 with another amino acid (having at position 86 a threonine instead of a serine residue), which retain ability bind to hp55-TNF-R, but have substantially lost ability to bind hp75-TNF-R. This invention is also directed to hTNF muteins which retain biological activity mediated by hp55-TNF-R, while no longer binding to hp75-TNF-R. However, the hTNF muteins of the present invention are not restricted to this type of mutein. Muteins of another type binding exclusively to hp55-TNF-R but having lost the capacity to elicit a functional cell response are also included.

In accordance with this invention the hTNF muteins by virtue of substitution at least at position 86 bind more strongly to hp55-TNF-R than to hp75-TNF-R.

BRIEF DESCRIPTION OF THE FIGURES

The following abbreviations and symbols used are: B, E, H, S, Xb and X which indicate cleavage sites for restriction enzymes B gII, EcoRI, HindIII, SalI, XbaI and XhoI, respectively. represents the regulatable promoter/operator element N25OPSN25OP29, represents the synthetic ribosomal binding site RBSII,SphI, represents genes for TNFα (TNFα), β-lactamase (bla), chloramphenicol acetyltransferase (cat), lac repressor (lacI) and neomycin phosphotransferase (neo), represents transcriptional terminators $t_o$ of phage lambda ($t_o$) and T1 of the *E. coli* rrnB operon (T1)⇆ represents the replication regions of plasmids pBR322 and pREP4 (repl.),→ represents the coding region under control of N25

OPSN25OP29 and RBSII,SphI.

Figure 1A:
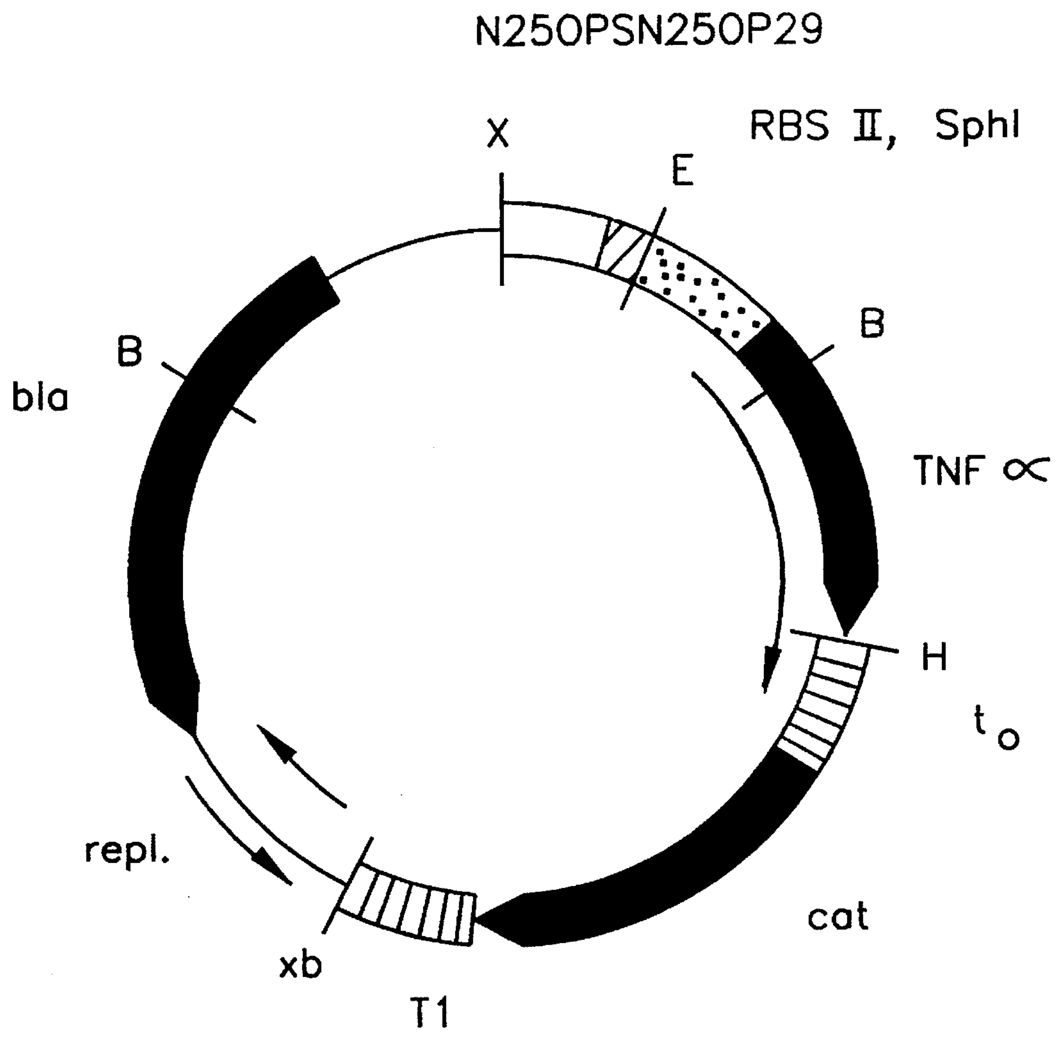
FIG. 1*a* is a schematic drawing of the plasmid pDS56/RBSII,SphI-TNFα.

FIGS. **1*b*-1 through 1*b*-4 displays the complete nucleotide sequence of plasmid pDS56/RBSII,SphI-TNFα. In this sequence, the recognition sequences of the restriction enzymes depicted in FIG. 1*a*** are indicated. The amino acid sequence shown represents in the three letter code the sequence of the mature TNFα (157 amino acids). [SEQ ID: 1]

FIG. **2*a*** is a schematic drawing of the plasmid pREP4.

Figure 2A:
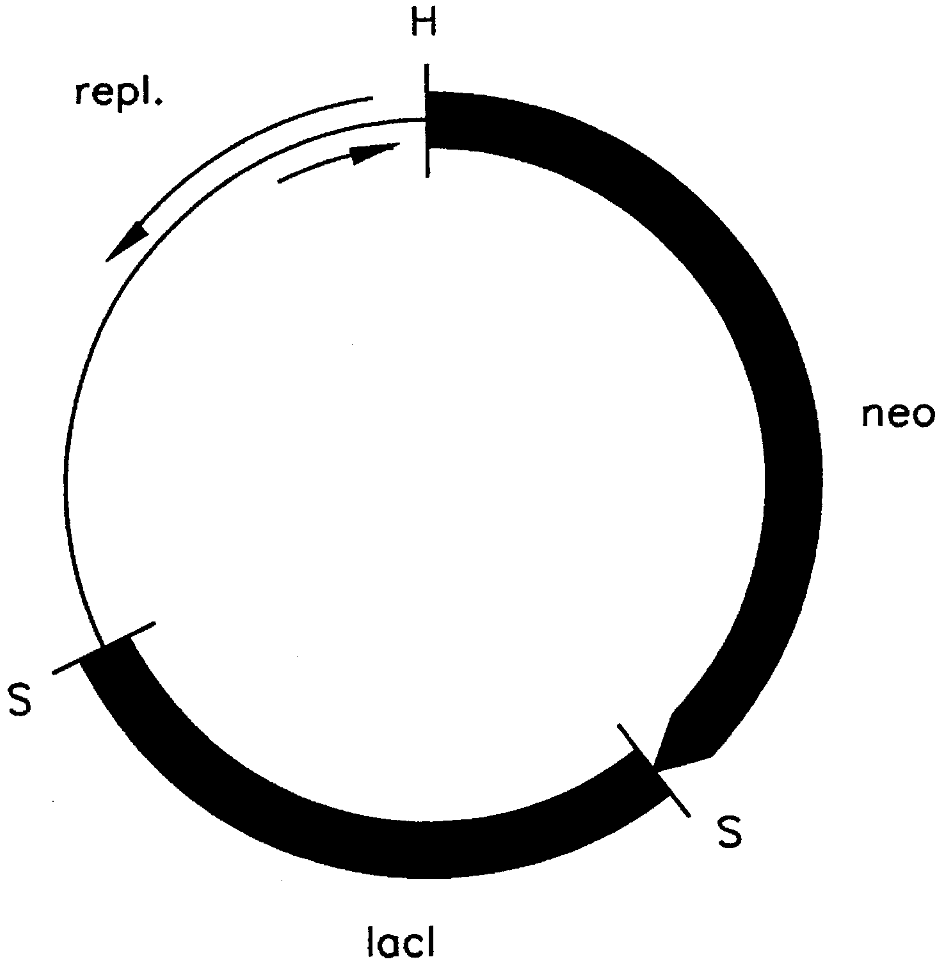

FIGS. **2*b*-1 through 2*b*-3 displays the complete nucleotide sequence of plasmid pREP4. In this sequence, the recognition sequences of the restriction enzymes depicted in FIG. 2*a*** are indicated. [SEQ ID: 3]

Figure 3:
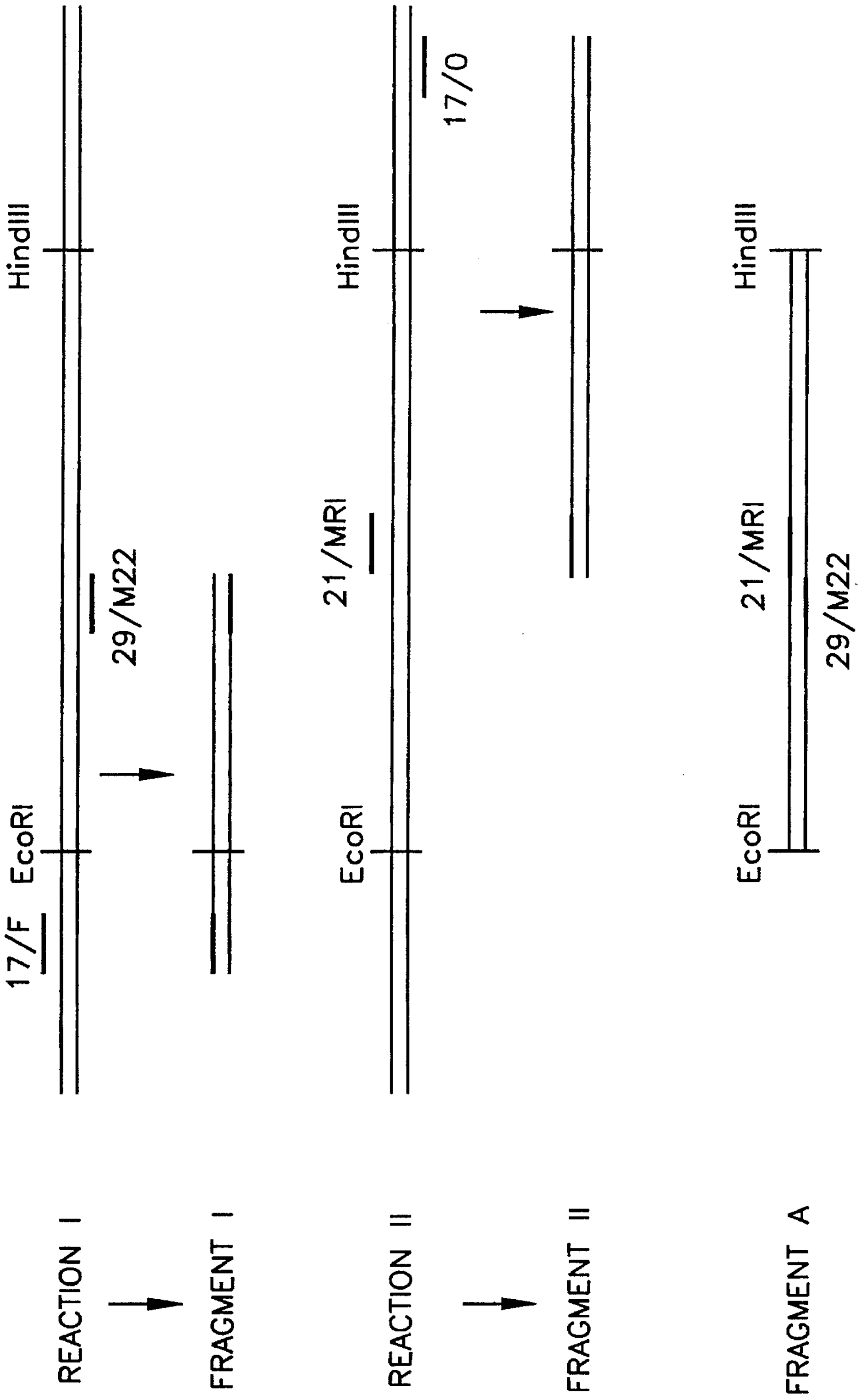

FIG. 3 outlines the preparation of an EcoRI-HindlII fragment encoding the TNFα mutein $Thr^{86}$-TNFα.

FIG. 4 displays the nucleotide sequence of Fragment 1 of plasmid pDS56/RB SII,SphI-INFα(Trp32) [SEQ ID: 4]

FIG. 5 displays the nucleotide sequence of Fragment 1 of plasmid "pDS56/RBSII,SphI-TNFα(Ser29) [SEQ ID: 6]

FIG. 6 displays the nucleotide sequence of Fragment 1 of plasmid pDS56/RBSII,SphI-TNFα(Ser29Trp32) [SEQ ID: 8]

Figure 7A:
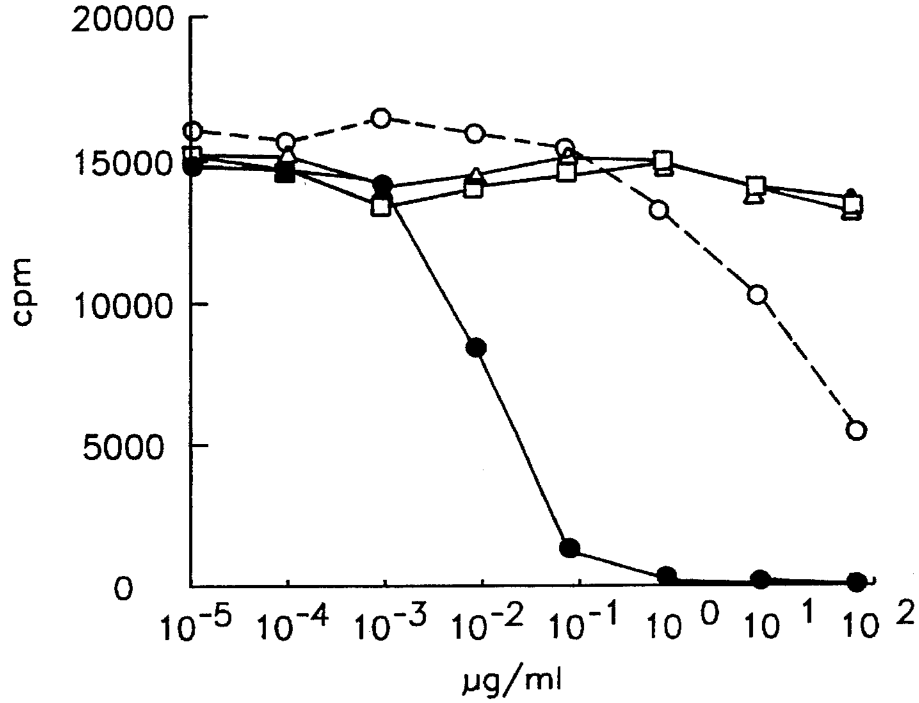
Figure 7B:
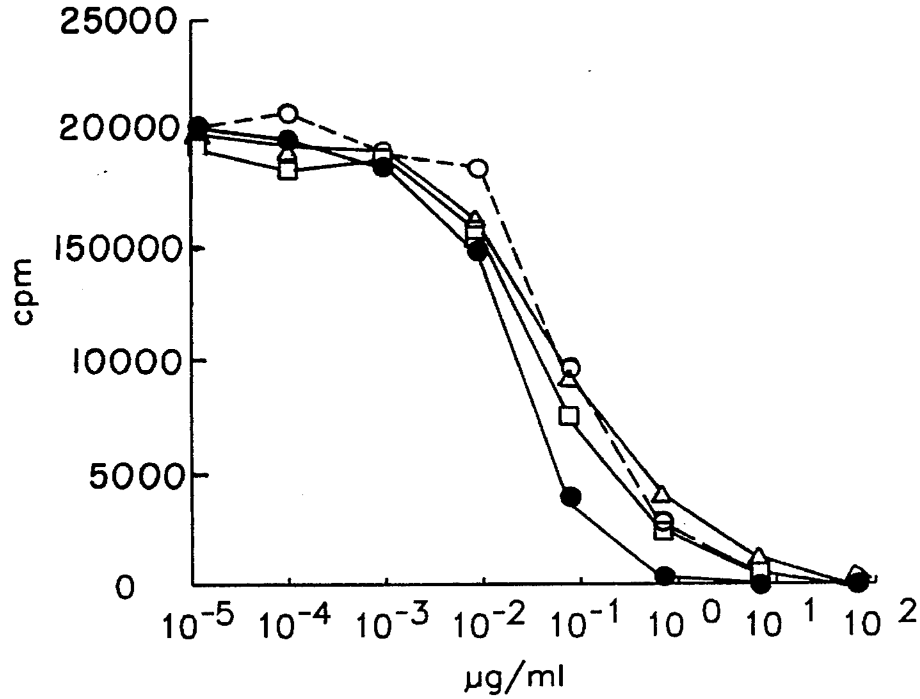

FIGS. 7A and 7B Competitive binding of wild-type human TNFα and $Thr^{86}$, $Trp^{32}$-$Thr^{86}$ and $Ser^{29}$-$Trp^{32}$-$Thr^{86}$ muteins to recombinant human p-75 and p-55 TNF-R's.

FIG. **7*b* Microtiter plates coated with recombinant human p-75TNF-R-IgGγ3 fusion protein (FIG. 7A) and recombinant human p-55TNF-R-IgGγ3 fusion protein (FIG. 7**B) were incubated with radiolabelled human TNFα in the presence of different concentrations of wild-type TNFα (closed circles), $Thr^{86}$ mutein (open circles), $Trp^{32}$-$Thr^{86}$ mutein (open squares) and $Ser^{29}$-$Trp^{32}$-$Thr^{86}$ mutein (open triangles). After three hours at room temperature bound radioactivity was counted in a γ-counter.

Figure 8A:
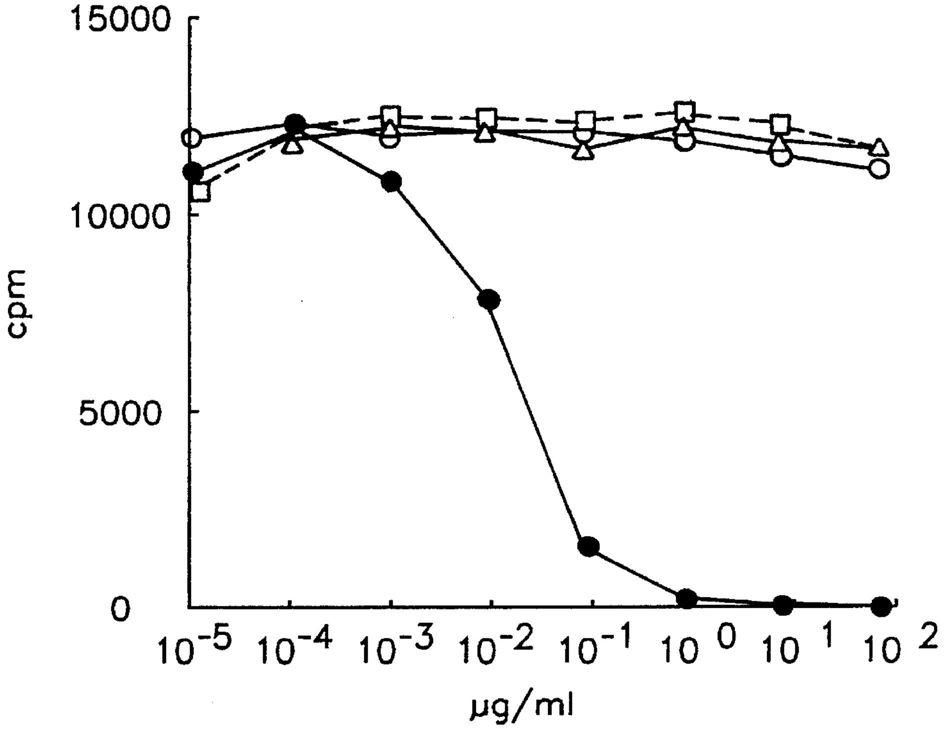
Figure 8B:
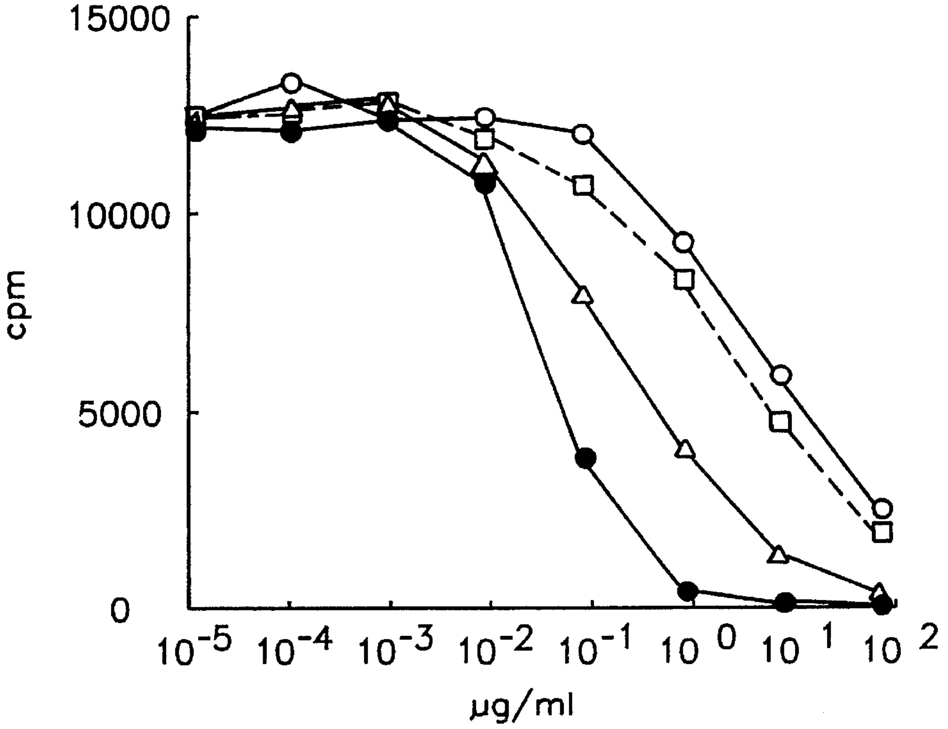

FIGS. 8A and 8B Competitive binding of wild-type human TNFα and $Ser^{29}$-$Thr^{86}$ $Glu^{31}$-$Thr^{86}$ and $Asn^{31}$-$Thr^{32}$-$Thr^{86}$ muteins to recombinant human p-75 and p-55TNF-R's.

FIG. **8*b* Microtiter plates coated with recombinant human p-75TNF-R-IgGγ3 fusion protein (FIG. 8A) and recombinant human p-55TNF-R-IgGγ3 fusion protein (FIG. 8**B) were incubated with radiolabelled human TNFα in the presence of different concentrations of wild-type TNFα (closed circles), $Ser^{29}$-$Thr^{86}$ mutein (open circles), $Asn^{31}$-$Thr^{32}$-$Thr^{86}$ mutein (open squares) and $Glu^{31}$-$Thr^{86}$ mutein (open triangles). After three hours at room temperature bound radioactivity was counted in a γ-counter.

DETAILED DESCRIPTION OF THE INVENTION

The present invention provides human Tumor Necrosis Factor muteins or pharmaceutically acceptable salts thereof, having selective binding affinity for the p55 subunit of human Tumor-Necrosis-Factor-Receptor (hp55-TNF-R) characterized in that the amino acid sequence of human Tumor Necrosis Factor is changed at least at position 86, having a threonine instead of a serine residue at this position. By selective binding is meant that the muteins of this invention bind to the p55 subunit (hp55-TNF-R) without any substantial binding to the p75 subunit (hp75-TNF-R).

The amino acid sequence of human TNF-α as disclosed by Pennica et al. [s.a.] is as follows:

| | | | | | | | | | | | | | | |
|---|---|---|---|---|---|---|---|---|---|---|---|---|---|---|
| 1 | | | | | | | | | 10 | | | | | |
| VAL | ARG | SER | SER | SER | ARG | THR | PRO | SER | ASP | LYS | PRO | VAL | ALA | HIS |
| | | | | 20 | | | | | | | | | 29 | 30 |
| VAL | VAL | ALA | ASN | PRO | GLN | ALA | GLU | GLY | GLN | LEU | GLN | TRP | LEU | ASN |
| 31 | 32 | | | | | | | | 40 | | | [SEQ ID: 2] | | |
| ARG | ARG | ALA | ASN | ALA | LEU | LEU | ALA | ASN | GLY | VAL | GLU | LEU | ARG | ASP |
| | | | | 50 | | | | | | | | | | 60 |
| ASN | GLN | LEU | VAL | VAL | PRO | SER | GLU | GLY | LEU | TYR | LEU | ILE | TYR | SER |
| | | | | | | | | | 70 | | | | | |
| GLN | VAL | LEU | PHE | LYS | GLY | GLN | GLY | CYS | PRO | SER | THR | HIS | VAL | LEU |
| | | | | 80 | | | | | | 86 | | | | 90 |
| LEU | THR | HIS | THR | ILE | SER | ARG | ILE | ALA | VAL | SER | TYR | GLN | THR | LYS |
| | | | | | | | | | 100 | | | | | |
| VAL | ASN | LEU | LEU | SER | ALA | ILE | LYS | SER | PRO | CYS | GLN | ARG | GLU | THR |
| | | | | 110 | | | | | | | | | | 120 |
| PRO | GLU | GLY | ALA | GLU | ALA | LYS | PRO | TRP | TYR | GLU | PRO | ILE | TYR | LEU |
| | | | | | | | | | 130 | | | | | |
| GLY | GLY | VAL | PHE | GLN | LEU | GLU | LYS | GLY | ASP | ARG | LEU | SER | ALA | GLU |
| | | | | 140 | | | | | | | | | | 150 |
| ILE | ASN | ARG | PRO | ASP | TYR | LEU | ASP | PHE | ALA | GLU | SER | GLY | GLN | VAL |
| | | | | | | 157 | | | | | | | | |
| TYR | PHE | GLY | ILE | ILE | ALA | LEU | | | | | | | | |

(also disclosed by Marmenout et al. (s.a.) or Wang et al. (s.a.) or Shirai et al.) or more specifically as coded for by the nucleotide sequence of the insert of the plasmid pDS56/RBSII,SphI-TNFα (see FIGS. **1*a* and 1*b*** and Example I), which insert sequence codes for mature TNF-α.

The hTNF muteins as defined above may have amino acids that differ from the amino acids at the same positions in hTNF at one or more positions in addition to 86, preferably at one or two additional positions, whereby positions 29, 31, 32, 29 and 32, or 31 and 32 are especially preferred individually or in any combination. Any amino acid, preferably any naturally occurring one, can be used at these additional positions. The amino acid sequence of these preferred hTNF muteins is as follows:

| | | | | | | | | | | | | | | |
|---|---|---|---|---|---|---|---|---|---|---|---|---|---|---|
| 1 | | | | | | | | | 10 | | | | | |
| VAL | ARG | SER | SER | SER | ARG | THR | PRO | SER | ASP | LYS | PRO | VAL | ALA | HIS |
| | | | | 20 | | | | | | | | | 29 | 30 |
| VAL | VAL | ALA | ASN | PRO | GLN | ALA | GLU | GLY | GLN | LEU | GLN | TRP | $X_1$ | ASN |
| 31 | 32 | | | | | | | | 40 | | | | | |
| $X_2$ | $X_3$ | ALA | ASN | ALA | LEU | LEU | ALA | ASN | GLY | VAL | GLU | LEU | ARG | ASP |
| | | | | 50 | | | | | | | | | | 60 |
| ASN | GLN | LEU | VAL | VAL | PRO | SER | GLU | GLY | LEU | TYR | LEU | ILE | TYR | SER |
| | | | | | | | | | 70 | | | | | |
| GLN | VAL | LEU | PHE | LYS | GLY | GLN | GLY | CYS | PRO | SER | THR | HIS | VAL | LEU |
| | | | | 80 | | | | | | 86 | | | | 90 |
| LEU | THR | HIS | THR | ILE | SER | ARG | ILE | ALA | VAL | THR | TYR | GLN | THR | LYS |
| | | | | | | | | | 100 | | | | | |
| VAL | ASN | LEU | LEU | SER | ALA | ILE | LYS | SER | PRO | CYS | GLN | ARG | GLU | THR |
| | | | | 110 | | | | | | | | | | 120 |
| PRO | GLU | GLY | ALA | GLU | ALA | LYS | PRO | TRP | TYR | GLU | PRO | ILE | TYR | LEU |
| | | | | | | | | | 130 | | | | | |
| GLY | GLY | VAL | PHE | GLN | LEU | GLU | LYS | GLY | ASP | ARG | LEU | SER | ALA | GLU |
| | | | | 140 | | | | | | | | | | 150 |
| ILE | ASN | ARG | PRO | ASP | TYR | LEU | ASP | PHE | ALA | GLU | SER | GLY | GLN | VAL |
| | | | | | | 157 | | | | | | | | |
| TYR | PHE | GLY | ILE | ILE | ALA | LEU [SEQ ID: 17], where | | | | | | | | |

$X_1$, $X_2$, and $X_3$ represent any amino acid. Therefore, in the muteins of this invention position 29 may be Leu while 30 and 32 are X, or position 29 may be X, while position 30 is Arg and 32 is X, or any other combination of wild-type amino acids or substituted amino acids at these three positions.

In the muteins of this invention, for substitutions at position 29 serine, glycine or tyrosine are preferred and serine is especially preferred. For substitutions at position 31 glutamic acid or asparagine are preferred. For substitutions at position 32 tyrosine, tryptophan or threonine are preferred, and tryptophan and threonine are specifically preferred.

Especially preferred hTNF muteins of the present invention are $Thr^{86}$-TNF-α, $Ser^{29}$-$Thr^{86}$-TNF-60 , $Glu^{31}$-$Thr^{86}$-TNF-α, $Trp^{32}$-$Thr^{86}$-TNF-α, $Ser^{29}$-$Trp^{32}$-$Thr^{86}$-TNF-α or $Asn^{31}$-$Thr^{32}$-$Thr^{86}$-TNF-α.

The hTNF muteins of the present invention may contain further amino acid substitutions if such substitutions do not alter their selective binding affinity for the p55-TNF-R. Amino acid substitutions in proteins and polypeptides which do not essentially alter biological activity are known in the art and described, e.g. by H. Neurath and R. L. Hill in "The Proteins", Academic Press, New York (1979), in particular in FIG. 6 of page 14. The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly and vice versa. The hTNF muteins of the present invention may additionally contain sequences of several amino acids which are coded for by "linker" sequences. These sequences may come from the expression vectors used for expression of the hTNF muteins of the invention.

The hTNF muteins of the present invention can also contain specific sequences that preferably bind to an affinity carrier material. Examples of such sequences are sequences containing at least two adjacent histidine residues (see in this respect European Patent Publication No. 282 042). Such sequences bind selectively to nitrilotriacetic acid nickel chelate resins (Hochuli and Döbeli, Biol. Chem. Hoppe-Seyler 368, 748 (1987); European Patent Publication No. 253 303). hTNF muteins which contain such a specific sequence can be linked either to the C-terminus or the N-terminus, or to both termini, of the hTNF-mutein amino acid sequences.

The hTNF muteins of the present invention can also be combined with different immunoglobulin heavy chain or light chain polypeptides. This leads to chimaeric hTNF mutein immunoglobulin polypeptides which could have increased half-life in vivo. Increased half-life in vivo has been shown for chimetic polypeptides consisting of the first two domains of the constant regions of the heavy chain or the light chain of a mammalian immunoglobulin (see Traunecker et al., Nature 331, 84–86 [1988] and European Patent Publication No. 394 827).

The hTNF muteins can also be coupled to polymers such as polyethylene glycol or polypropylene glycol having a molecular weight of 500 to 20,000 daltons. This leads to protected hTNF mutein compositions which could be substantially non-immunogenic. Several modes of coupling the polymer with the polypeptide are available and described, e.g., in U.S. Pat. No. 4,179,337.

The hTNF muteins of the present invention can be produced by recombinant methods known in the art and described e.g. in Sambrook et al. [Molecular Cloning, A Laboratory Manual, 2nd ed., Cold Spring Harbour Laboratory, Cold Spring Harbour Laboratory Press, USA (1989)]

and in the following paragraphs. Assays to determine the selective binding affinity for p55-TNF-R of such hTNF muteins are described below and in the Examples. Alternatively, the muteins of the present invention can be chemically synthesized using standard methods known in the art, preferably solid state methods, such as the methods of Merrifield (J. Am. Chem. Soc. 85, 2149–2154 [1963]). Salts of such muteins are also an object of the present invention. Such salts can be produced by methods known in the art.

Separating beneficial from unwanted TNF-α activities by using compounds specifically binding to one or the other TNF-receptor, such as the hTNF muteins of the present invention, can be used in general in any disease states where TNF plays a role as described below.

Polynucleotides comprising a coding DNA sequence coding for hTNF-muteins as hereinbefore described or comprising DNA sequences which are complementary to such coding sequences are also an object of the present invention. Such DNA sequences can be constructed starting from genomic or cDNA sequences coding for hTNF as disclosed in the art [s.a.] using known methods of in vitro mutagenesis [see e.g. Sambrook et al., 1989]. Preferred polynucleotides comprise DNA sequences coding for proteins comprising the amino acid sequence of hTNF-α but with Thr at position 86 ($Thr^{86}$TNF-α), or additionally with Gly, Set, or Tyr at position 29, preferably Ser ($Ser^{29}Thr^{86}$TNF-α) or with Glu or Asn at position 31, preferably Glu ($Glu^{31}Thr^{86}$TNF-α), or with Tyr, Trp or Thr at position 32, preferably Trp or Thr, most preferably Trp ($Trp^{29}Thr^{86}$TNF-α), or with Ser at position 29 and Trp at position 32 ($Ser^{29}Trp^{32}Thr^{86}$TNF-α), or with Asn at position 31 and Thr at position 32 ($Asn^{31}Thr^{32}Thr^{86}$TNF-α), and the DNA sequences complementary to such sequences. DNA sequences of this invention include DNA sequences coding for an hTNF mutein with selective binding affinity for hp55-TNF-R, which mutein comprises the sequence of hTNFα with a Thr at position 86 instead of a Set, and additional substitutions which do not alter the selective binding properties of the mutein encoded.

The DNA sequences coding for the proteins are useful as intermediates in the production of said proteins, as further described below.

DNA sequences of this invention may be obtained from vectors containing those sequences as described herein, or from vectors containing the DNA sequence of hTNF-α as disclosed in the art which are mutagenized as described below. Alternatively, such DNA sequences may be derived using the genetic code from the amino acid sequences of the proteins of this invention and chemically synthesized by methods known in the art.

Such mutagenesis can be carried out at random in order to obtain a large number of mutants which can then be tested for their desired properties in appropriate assay systems. Alternatively, defined positions in a given DNA sequence can be mutated by so called site directed mutagenesis [see e.g. Sambrook et al., 1989, 15.51–15.113] or by mutagenesis using the polymerase chain reaction [see e.g. White et al., Trends in Genetics 5, 185–189 (1989)].

One chemical mutagen which is often used for random mutagenesis is sodium bisulfite, which converts a cytosine residue into an uracil residue and hence leads to a transition of "C" to "T" (standard abbreviations for nucleotides) [for the method see e.g. Shortle and Nathans, Proc. Nat. Acad. Sci. U.S.A. 75, 2170–2174 (1978) or Pine and Huang, Meth. Enzym. 154, 415–430 (1987)]. This mutagen acts solely on single stranded DNA. However, the mutated target DNA sequence is expressed in a double stranded plasmid vector. To avoid the necessity of recloning from mutagenesis to expression vectors, so called "phasmids" may be used. These are vectors which, in addition to a plasmid origin of replication, carry an origin of replication derived from a filamentous phage. Examples of such phasmids are the pMa- and pMc-phasmids as described by Stanssen et al. [Nucleic Acids Res. 17, 4441–4454, (1989)]. Using this expression system one can construct so called "gap-duplex"-structures [see also Kramer et al., Nucl. Acids. Res. 12, 9441–9456 (1984)] where only the TNF-coding sequence (s.a.) is in a single stranded configuration and therefore accessible to the specific chemical mutagen. "Gap-duplexes" to be used in random mutagenesis can be constructed as described for site-specific mutagenesis by Stanssen et al. [s.a.] that the (−)strand contains the same active antibiotic resistance gene as the (+)strand. By making use of different restriction sites in the DNA-sequence encoding hTNFα, variation of the width of the gap is possible. Examples of such restriction sites are the C1a1-Sal1 sites (470 nucleotides), BstX1—BstX1 sites (237 nucleotides) or Sty1-Sty1 sites (68 nucleotides). Such gap-duplex-constructs can then be treated with increasing concentrations (up to 4M) of bisulfite, followed by several dialysis steps, as described by Shortle and Nathans (s.a.). A suitable procaryotic host cell can then be transformed by such phasmid constructs according to methods known in the art and described e.g. by Sambrook et al. (s.a.). A suitable procaryotic host cell means in this context a host cell deficient in a repair function so that a mutated residue is maintained in the DNA during replication and which host cell is capable of expressing the corresponding mutated TNF. For example, the host cell may be deficient in a specific repair function such that a uracil residue is maintained as a mutation. Such specific host strains are known in the art, for example for *E. coli* strains, e.g. *E. coli* BW 313 [Kunkel, T. A., Proc. Natl. Acad. Sci. USA 82, 488–492 (1985)]. The resulting clones can then be screened for those expressing a desired hTNF mutein by appropriate assay systems as described below. For example each colony can be inoculated in a microtiter plate in a suitable medium containing the relevant antibiotic. The cells may be lysed by addition of lysozyme, followed by sequential freeze-thaw cycles. After precipitation of nucleic acids and centrifugation, the supernatant of each colony can directly be used in appropriate assays as described, e.g., in Example IIa and IIb or Example VIII measuring binding to the p75-TNF-R and the p55-TNF-R on the surface of living cells or in purified form.

If desired, the specific sites of mutation can be determined, for example by restriction fragment analysis [see e.g. Sambrook et al. (s.a.)]. By determination of the DNA sequence of such fragments the exact position of the mutation can be determined and if such mutation leads to an amino acid replacement the new amino acid can be deduced from the determined DNA sequence. DNA sequencing can be performed according to methods known in the art, for example, by using T7 polymerase on supercoiled DNA with a commercially available sequencing kit (Pharmacia, Uppsala, Sweden).

As already mentioned above, another possibility for mutating a given DNA sequence is by "site directed mutagenesis". A widely used strategy for such mutagenesis as originally outlined by Hutchinson and Edgell [J. Virol. 8, 181 (1971)] involves the annealing of a synthetic oligonucleotide carrying the desired nucleotide substitution to a target region of a single-stranded DNA sequence wherein the mutation should be introduced [for review see Smith, Annual. Rev. Genet. 19, 423 (1985) and for improved methods see references 2–6 in Stanssen et al. (1989)].

One preferred method is that of Stanssen et al. (1989) using "gapped duplex DNA" as originally described by Kramer et al. (1984) [see above and Kramer and Fritz, Methods in Enzymology, (1987), Academic Press, Inc., USA] but using antibiotic resistance genes instead of M13 functional genes for selection of the mutated strand in addition to the phasmid technology as also described by Stanssen et al. (1989) [s.a.]. An advantage of this method is that successive cycles of mutagenesis can be performed without the need to transfer the gene to a new mutagenesis vector: second round mutagenesis differs only in the selection to another antibiotic marker (Stanssen et al., s.a.). As a control, site-specific back mutagenesis of the mutant to the wild-type TNF can be used. In addition, the use of an oligonucleotide to create or destroy a restriction site in the TNF gene, allows control of the mutant not only by hybridization to the oligonucleotide used for site directed mutagenesis but also by the presence or absence of the restriction site. In order to create a set of hTNF muteins with wild-type amino acids replaced by any naturally occurring amino acid at a defined position of their amino acid sequence a set of oligonucleotides is used with all possible codons at the defined position.

As mentioned above, another possibility of mutating a given DNA sequence is mutagenesis by using the polymerase chain reaction (PCR). The principles of this method are outlined by White et al. (1989), and improved methods are described in Innis et al. [PCR Protocols: A Guide to Methods and Applications, Academic Press, Inc. (1990)].

PCR is an in vitro method for ,producing large amounts of a specific DNA fragment of defined length and sequence from small amounts of a template DNA. PCR is based on the enzymatic amplification of the DNA fragment which is flanked by two oligonucleotide primers that hybridize to opposite strands of the target sequence. The primers are oriented with their 3' ends pointing towards each other. Repeated cycles of heat denaturation of the template, annealing of the primers to their complementary sequences and extension of the annealed primers with a DNA polymerase result in the amplification of the segment between the 5' ends of the PCR primers. Since the extension product of each primer can serve as a template for the other, each cycle essentially doubles the s amount of the DNA fragment produced in the previous cycle. Since the primers are physically incorporated into the amplified product and mismatches between the 5' end of the primer and the template do not significantly affect the efficiency of the amplification, it is possible to alter the amplified sequence thereby introducing the desired mutation into the amplified DNA. By utilizing the thermostable Taq DNA polymerase isolated from the thermophilic bacteria *Thermus aquaticus*, it has been possible to avoid denaturation of the polymerase which necessitated the addition of enzyme after each heat denaturation step. This development has led to the automation of PCR by a variety of simple temperature-cycling devices. In addition, the specificity of the amplification reaction is increased by allowing the use of higher temperatures for primer annealing and extension. The increased specificity improves the overall yield of amplified products by minimizing the competition by non-target fragments for enzyme and primers.

Design and synthesis of oligonucleotides can be effected as known in the art and described e.g. in Sambrook et al. (1989) or in one of the references cited above with respect to site directed mutagenesis.

As soon as a DNA sequence coding for a hTNF-mutein of the present invention has been created, expression can be effected by the phasmid technology as described above or by use of any suitable proor eukaryotic expression system well known in the art [see e.g. Sambrook et al., s.a.].

Expression is effected preferably in prokaryotic cells, e.g., in *E. coli, Bacillus subtilis* and so on, whereby *E. coli*, specifically *E. coli* K12 strains e.g. M15 [described as DZ 291 by Villarejo et al. in J. Bacteriol. 120, 466–474 (1974)], HB 101 [ATCC No. 33694], WK6 (Stranssens et al. s.a.) or *E. coli* SG13009 [Gottesman et al., J. Bacteriol. 148, 265–273 (1981)] are preferred. Expression of the hTNF muteins of the present invention can also be effected in lower or higher eukaryotic cells, for example yeast cells (Saccharomyces, Pichia etc.), filamentous fungi (Aspergillus etc.) or cell lines (chinese hamster ovary cell lines etc.). Expression in yeast cells is preferred [see Sreekrishna et al., Biochem. 28, 4117–4125, (1989); Hitzeman et al., Nature 293, 717–722 (1981); European Patent Publication No. 263 311]. Expression of the hTNF muteins of the present invention may occur in such systems either intracellularly, or, after suitable adaption of the gene, extracellularly (see Leemans et al., Gene 85, 99–108, 1989).

Suitable vectors used for expression in *E. Coli* are mentioned by Sambrook et al. [s.a.] or by Fiers et al. in "Proc. 8th Int. Biotechnology Symposium" [Soc. Franc. de Microbiol., Pads, (Durand et al., eds.), pp. 680–697 (1988)] and more specifically vectors of the pDS family [Bujard et al., Methods in Enzymology, eds. Wu and Grossmann, Academic Press, Inc. Vol. 155, 416–433 (1987); Stüber et al., Immunological Methods, eds. Lefkovits and Pernis, Academic Press, Inc., Vol. IV, 121–152 (1990)] for example pDS56/RBSII,SphI-TNFα(Thr86) (see Example I) or pDS56/RBSII,SphI-TNFα(Trp32Thr86) (see Example III) or pDS56/RBSII,SphI-TNF*a* (Ser29Thr86) or pDS56/RBSII,SphI-TNFα(Ser29Trp32Thr86) or pDS56/RBSII,SphI-TNFα(Asn31Thr32Thr86) or pDS56/RBSII,SphI-TNFα(Glu31Thr86) (see Example IV). Since these specific pDS56/RBSII-plasmids achieve a high level of expression due to their specific regulatable promoter/operator elements and ribosomal binding sites the plasmids can be maintained in *E. coli* cells only when the activity of the promoter/operator element is repressed by the binding of a lac repressor to the operator. The activity of the promoter can be restored at the desired cell density by addition of IPTG, which inactivates the repressor and clears the promoter. Since most of the *E. coli* strains do not provide enough repressor molecules to completely repress the function of the promoter sequences present in these high copy number plasmids, such *E. coli* strains, like *E. coli* M15 or SG13009, have to be transformed at first with a plasmid, like pREP 4 (see FIGS. 2*a* and *b*), coding for the lac repressor, before being transformed with the specific pDS56/RBSII-plasmids of the invention which can then be stably maintained in the *E. coli* cells. Beside coding for the lac repressor, pREP4 contains also a region of the plasmid pACYC184 [Chang and Cohen, J. Bacteriol. 134, 1141–1156 (1978)], which contains all information required for replication and stable transmission to daughter cells [for additional information see also "System for high level production in *E. coli* and rapid purification of recombinant proteins: application to epitope mapping, preparation of antibodies and structure function analysis" by Stüber et al. in Immunological Methods, Vol. IV, pp 121–152, Lefkovits and Pernis (eds.), Academic Press, New York (1990)].

Transformation of the host cells by vectors as described above may be carried out by any conventional procedure [see for example Sambrook et al. (s.a.)]. Where the host cell is a prokaryote such as *E. coli*, competent cells which are capable of DNA uptake are prepared from cells harvested after exponential growth phase and subsequently treated according to the known $CaCl_2$-method. Transformation can also be performed after forming a protoplast of the host cell or by other methods known in the art and described, e.g., in Sambrook et al. (s.a.). Therefore a vector, especially for expression in a prokaryotic or lower eukaryotic host cell, comprising a DNA sequence coding for an hTNF mutein as described above, and a host cell, especially a prokaryotic host cell, e.g. *E. coli*, or a lower eukaryotic host cell, transformed by such a vector are also an object of the present invention.

Usually, the host organisms which contain a desired expression vector are grown under conditions which are optimal for their growth. In case of a procaryotic host at the end of the exponential growth, when the increase in cell number per unit time decreases, the expression of the desired hTNF mutein is induced, i.e. the DNA coding for the desired hTNF mutein is transcribed and the transcribed mRNA is translated. The induction can be carried out by adding an inducer or a derepressor to the growth medium or by altering a physical parameter, e.g. a change in temperature. In the expression vectors used in the preferred embodiments of the present invention, the expression is controlled by the lac repressor. By adding isopropyl-β-D-thiogalactopyranoside (IPTG), the expression control sequence is derepressed and the synthesis of the desired hTNF mutein is thereby induced.

The hTNF muteins of the present invention produced by transformed host cells as stated above can be recovered from the culture medium or after opening the cells and/or extraction by any appropriate method known in protein and peptide chemistry such as, precipitation with ammonium sulfate, dialysis, ultrafiltration, gel filtration or ion-exchange chromatography, gel electrophoresis, isoelectric focusing, affinity chromatography (immunoaffinity chromatography, HPLC or the like). Specifically preferred methods are precipitation with ammonium sulfate and/or polyethylenimine, dialysis, affinity chromatography, e.g. on phenyl-agarose, specifically phenyl-sepharose, or ion-exchange chromatography, specifically on a MONO-Q-and/or MONO-S-matrix (Pharmacia, Uppsala, Sweden) or more specifically are those as described by Tavernier et al. [J. Mol. Biol. 211, 493–501 (1990)] and those disclosed in Example V.

It is therefore also an object of the present invention to provide a process for the preparation of hTNF muteins as specified above which process comprises cultivating a transformed host cell as described above in a suitable medium and isolating a mutein from the culture supernatant or the host cell itself, and if desired converting said mutein into a pharmaceutically acceptable salt. The compounds whenever prepared according to such a process are also an object of the present invention.

The hTNF muteins of the present invention are characterized by showing a selective binding affinity for human p55-TNF-R. Such property can be determined by any assay known in the art for measuring binding affinities. For example the binding of TNF itself and of the muteins of the present invention can be measured using cells in cell culture which express the two types of TNF-receptors to a different degree, for example Hep-2 cells which exclusively express the human p55-TNF-R, and U937 or HL60 cells which express in addition the human p75-TNF-R [see Brockhaus et al., Proc. Nat. Acad. Sci. U.S.A. 87, 3127–3131, (1990); Hohmann et al., J. Biol. Chem. 264, 14927–14934, (1989); Loetscher et al. (1990); Dembic et al. (1990)]. Of course binding affinities can also be determined directly by using purified native or recombinant p55-TNF-R and p75-TNF-R as specifically described in the Examples, or by using the corresponding soluble analogs of such receptors.

The term selective binding affinity for the human p55-Tumor-Necrosis-Factor-Receptor" refers in the context of the present invention to a difference in binding affinities to the two types of TNF-receptors which is with respect to the assay system used significant enough to say that a mutein of the present invention binds selectively to the p55TNF-Receptors similarly to wild-type TNF but has essentially lost functionally relevant binding to hp75-TNF-R. More o specifically this term means in the context of the assay system of the Examples that a $K_D$ value of a specific hTNF mutein of the present invention is at least a factor of 10 or more, especially preferred at least a factor of $10^2$, larger than for wild-type TNF-α determined by using the in vitro binding assay with recombinant soluble hp75-TNF-R whereas its $K_D$ value determined by using the in vitro binding assay to recombinant soluble hp55-TNF-R for the same hTNF mutein differs not by more than a factor of 2 from that of wild-type TNF-α. It is however understood that these specific $K_D$ values are given for illustration and should not be considered as limiting in any manner. FIGS. 7 and 8 shows that the h-TNF muteins of this invention do not compete with TNF-α to bind p75-TNF-R, but do competitively bind p55-TNF-R.

The hTNF muteins of the present invention can be characterized by their anti-tumour activity by methods known in the art.

The hTNF muteins may be administered alone or with one or more additional compounds of the present invention in pharmaceutically acceptable oral, injectable or topical compositions and modes. Administration will be in a dosage such that the amount of the composition in the patient is effective to modify the biological function associated with hTNF mutein function.

Pharmaceutical compositions containing hTNF muteins in association with a compatible pharmaceutically acceptable carrier material are therefore a further object of the present invention. Any conventional carrier material can be utilized. The carrier material can be organic or inorganic, suitable for enteral, percutaneous or parenteral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavouring agents, preservatives, stabilizers, emulsifying agents, buffers and the like may be added in accordance with accepted practices of pharmaceutical compounding.

The pharmaceutical preparations can be made up in any conventional form including: a) a solid form of oral administration such as tablets, capsules, pills, powders, granules and the like; b) a liquid form for oral administration such as solutions, syrups, suspensions, elixirs and the like; c) preparations for parenteral administration such as sterile solutions, suspensions or emulsions; and d) preparations for topical administrations such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure and/or buffers.

Parenteral dosage forms may be infusions or injectable solutions which can be injected intravenously or intramuscularly. These preparations can also contain other medicinally active substances. Additional additives such as preservatives, stabilizers, emulsifying agents, buffers and the like may be added in accordance with accepted practices of pharmaceutical compounding.

Accordingly it is also an object of the present invention to provide a process for the preparation of a pharmaceutical composition which process is characterized in that a compound obtained by a process of the present invention and if desired, additional pharmaceutically active substances are mixed with a non-toxic, inert, therapeutically compatible carrier material and the mixture is brought into a galenical application form.

Furthermore the use of a compound prepared according to a process of the present invention for the preparation of a pharmaceutical composition as described above is also an object of the present invention.

Finally, antibodies can be raised against the hTNF muteins of the present invention. These antibodies can be used in a well-known manner for diagnostic or therapeutic purposes as well as for purification purposes. Such antibodies can be produced by injecting a mammalian or avian animal with a sufficient amount of a vaccine formulation comprising a hTNF mutein of the present invention and a compatible pharmaceutical carrier to elicit the production of antibodies against said hTNF mutein. The appropriate amount of the hTNF mutein which would be required would be known to one of skill in the art or could be determined by routine experimentation. As used in connection with this invention, the term "pharmaceutical carrier" can mean either the standard compositions which are suitable for human administration or the typical adjuvants employed in animal vaccinations. Monoclonal antibodies can be produced by fusing B-cells of immunized animals with myeloma cells by methods well known in the art, and screening the antibodies produced by the resulting hybridomaa for binding to the h-TFN-α mutein.

TNF is a potent pleiotropic cytokine. Its many different activities include acting as a growth factor for immune cells, as a mediator in inflammation, or as an inducer of specific genes in endothelium. These activities relate to host defense to infection and injury. TNF also exhibits high systemic toxicity; the deleterious effects of bacteriaemia and septic shock or of bacterial meningitis are mediated to a large extent by endogenous cytokines among which TNF has an early and important role. Furthermore, many cells and cell lines are sensitive to a direct cytotoxic activity of TNF. Various systemic effects and cellular toxicity presumably combine in the antitumor activity of TNF seen in animal studies.

These facts form the rational basis for the development of novel therapeutic strategies using the hTNF muteins of the present invention, where in particular the potential to dissect the many different hTNF activities is exploited to separate unwanted toxic from desired activities. For example, the hTNF muteins of the present inventions may be used as antitumor agents at high doses, which doses are made possible by the lower systemic toxicity. This would overcome the dose-limiting toxicity which presumably severely restricts the use of wild-type hTNF in cancer patients. However, the potential use of the hTNF muteins of the present invention is not restricted to cancer therapy. Any disease where TNF acts as host defense factor in bacterial infection [for example Kindler, V. et al., CELL 56, 731–740 (1989); Nakano, Y. et al., J. Immunol. 144, 1935, (1990)] or as a mediator in inflammation, would be alleviated with a 55kDa TNF receptor type specific drug such as the hTNF muteins of the present invention. TNF has also been shown to play a role in cachexia [e.g. Beutler, B. and Cerami, (sa)] and TNF muteins of the present invention with low systemic toxicity might be used for anti-obesity therapy. Even disease states characterised by the toxic activities exerted by excessive TNF release such as septic shock or bacterial meningitis can benefit from 55kDA TNF receptor specific agonists such as the muteins of the present invention above or in combination with TNF antagonists p55-TNF-Receptor type specific agonists with lower systemic toxicity than TNF, and selectively triggering only some of the many different TNF activities may be expected to have significant advantages when compared to wild-type TNF. A concise summary of the emerging role of TNF for novel therapies is [Tumor Necrosis Factors, The Molecules and their Emerging Role in Medicine, B. Beutler, ed., Raven Press, 1992, ISBN 0-88167-852-X]. This reference describes the activities of TNF in modulating endothelial cell homeostatic properties and neutrophil adhesion, tissue ischemia and reperfusion injury, on osteoblasts and osteoclasts in bone resorption, as growth factor on many cells in general and in hematopoiesis, as well as in metabolic and nutritional effects. TNF as growth/differentiation factor in the generation of lymphokine-activated killer (LAK) cells appears to contribute to the antitumor activities of TNF. p55-TNF-R controls induction of specific genes providing cellular protection mechanisms such as induction of Mn-superoxide dismutase [Lewis et al, Proc. Natl. Acad. Sci. USA 88, 2830 (1991); Tartaglia et al, Proc. Natl. Acad. Sci. USA 88, 9292 (1991)]. In view of the various important activities of TNF in combination with its direct cytotoxicity in some cells, novel therapeutic strategies using receptor type specific TNF agonists should prove to be important in treating a range of conditions.

An important aspect of this invention is that all these activities may o be enhanced or modulated in combination with other recombinant cytokines such as for example interferon-gamma.

The following Examples are intended to illustrate details of the invention, without thereby limiting it in any manner.

EXAMPLES

Unless otherwise specified, percentages given below for solids in solid mixtures, liquids in liquids and solids in liquids are on a wt/wt, vol/vol and wt/vol basis, respectively.

Example I

Preparation of $Thr^{86}$-TNFα

Plasmid pDS56/RBSII,SphI-TNFα

The human TNFα expression plasmid pDS56/RBSII, SphI-TNFα (see FIG. 1) was the source of the TNFα gene for preparation of the various TNFα muteins of this invention. The transformed *E. coli* strain M15 [pREP4;pDS56/RBSII,SphI-TNFα] has been deposited under the Budapest Treaty for patent purposes at the Deutsche Sammlung yon Mikroorganismen und Zellkulturen GmbH (DSM) in Braunschweig, BRD, at Sep. 8th, 1991, under the accession number DSM 6713.

Mutagenesis of the TNFα gene using PCR

Two PCR reactions were performed with plasmid pDS56/RBSII,SphI-TNFα (FIG. 1) as the template DNA using a Perkin-Elmer Cetus GeneAmp$^{TM}$ DNA Amplification Reagent Kit with AmpliTaq$^{TM}$ Recombinant Taq DNA Polymerase [see FIG. 3].

Reaction I was performed with primers 17/F (5'-GGCGTATCACGAGGCCCTTTCG-3']SEQ ID: 10]; primer 17/F comprises nucleotides 3949–3970 of plasmid pDS56/RBSII, SphI-TNFα) and 29/M22 (5 -GTAGGTGACGGCGATGCGGCTGATGGT-3'[SEQ ID: 15]; primer 29/M22 comprises nucleotides which are complementary to nucleotides 378–352 of plasmid pDS56/RBSII,SphI-TNFα, the mutated base is underlined).

Reaction II was performed with primers 29/MR1 (5'-CAGACCAAGGTCAACCTCCTC-3'[SEQ ID: 16]; primer 29/MR1 comprises nucleotides 379—399 of plasmid pDS56/RBSII,SphI-TNFα)and 17/O (5'-CATTACTGGATCTATCAACAGG-3'[SEQ ID: 11]; primer 17/O comprises nucleotides which are complementary to nucleotides 748–727 of plasmid pDS56/RBSII,SphI-TNFα).

In a typical experiment, 10 μl template DNA (10 ng), 5 μl each of the two primers (100 pmoles each), 16 μdNTP's mix (1.25 mM of dATP, dGTP, dCTP, and dTTP), 10 μl 10× reaction buffer (100 mM Tris-HCl pH 8.3, 500 mM KCL, 15 mM $MgCl_2$ and 0.1% gelatin), 1 μl (5 units) AmpliTaq$^{TM}$ DNA polymerase and 53 μl $H_2O$ were mixed in an Eppendorf tube and overlaid with 80 ml mineral oil (Perkin-Elmer Cetus). The tubes were transferred to a DNA thermal cycler (TRIO-Thermoblock, Biometra) and kept for 1 min at 94° C., before 35 cycles of melting the DNA (1 min at 94° C.), annealing the primers (1 min at 50° C.), and extending the primers (3 min at 72° C.) were performed. After additional 2 min at 72° C., the reactions were cooled to room temperature and extracted with chloroform. The DNA present in the aqueous phase was precipitated with ethanol and subjected to electrophoresis in a 6% polyacrylamide gel [Sambrook et al., 1989]. After staining of the DNA with ethidium bromide, fragments I and II (see FIG. 3) were isolated from the gel and purified [Sambrook et al., 1989].

Preparation of a DNA fragment encoding Thr$^{86}$-TNFα

Fragments I and II were enzymatically phosphorylated, before they were ligated with each other [Sambrook et al., 1989]. After heat-inactivation of the ligase and digestion with restriction enzymes EcoRI and HindIII, the DNA was subjected to electrophoresis in a 6% polyacrylamide gel. After staining of the DNA with ethidium bromide, the EcoRI-HindIII fragment A [see FIG. 3] was isolated from the gel and purified [s.a].

Preparation of a plasmid encoding Thr$^{86}$-TNFα

The EcoRI-HindIII fragment A was inserted according to standard methods [Sambrook et al., 1989] into the EcoRI-HindIII opened plasmid pDS56/RBSII,SphI-TNFα generating the plasmid pDS56/RBSII,SphI-TNFα(Thr86). Plasmid DNA was prepared [Birnboim et al., 1979] and the identity of the coding region for the TNFα mutein was confirmed by sequencing the double-stranded DNA [Sambrook et al., 1989].

Production of Thr$^{86}$-TNFα

Plasmid pDS56/RBSII,SphI-TNFα(Thr86) was transformed into *E. coli M*15 cells containing already plasmid pREP4 by standard methods [s.a.]. Transformed cells were grown at 37° C. in LB medium [Sambrook et al., 1989] containing 100 mg/l ampicillin and 25 mg/l kanamycin. At an optical density at 600 nm of about 0.7 to 1.0 IPTG was added to a final concentration of 2 mM. After additional 2.5 to 5 h at 37° C. the cells were harvested by centrifugation.

Example II

Preparation of Glu$^{31}$-TNFαand Asn$^{31}$Thr$^{32}$TNFα

Principles

The TNFα muteins Glu$^{31}$-TNFα and Asn$^{31}$Thr$^{32}$TNFα were prepared following the procedure described in detail in Example I for the preparation of Thr$^{86}$-TNFα. Therefore, in the description of the preparation of the TNFα muteins listed above only the primers used in PCR reactions I and II are specified. Furthermore, the names of the expression plasmids encoding the various TNFα muteins are given.

Preparation of Glu$^{31}$-TNFα

PCR reaction I was performed with primers 17/F (5'-GGCGTATCACGAGGCCCTTTCG-3'[SEQ ID: 10]; primer 17/F comprises nucleotides 3949–3970 of plasmid pDS56/RBSII,SphI-TNFα) and 21/M5 (5 -ATTGGCCCGCTCGTTCAGCCACTGGAGCTGCCCCTC-3'[SEQ ID: 12]; primer 21/M5 comprises nucleotides which are complementary to nucleotides 219–184 of plasmid pDS56/RBSII,SphI-TNFα, mutated bases are underlined). PCR reaction II was performed with primers 21/MR (5'-GCCCTCCTGGCCAATGGCGTGG-3'[SEQ ID: 14]; primer 21/MR comprises nucleotides 220–241 of plasmid pDS56/RBSII,SphI-TNFα) and 17/O (5' -CATTACTGGATCTATCAACAGG-3'[SEQ ID: 11]; primer 17/O comprises nucleotides which are complementary to nucleotides 748–727 of plasmid pDS56/RBSII,SphI-TNFα).

The resulting expression plasmid pDS56/RBSII,SphI-TNFα(Glu31) was used for production of Glu$^{31}$-TNFα and in the construction of plasmid pDS56/RBSII,SphI-TNFα(Glu31Thr86) (see Example IV).

Preparation of Asn$^{31}$Thr$^{32}$-TNFα

PCR reaction I was performed with primers 17/F (5'-GGCGTATCACGAGGCCCTTTCG-3'[SEQ ID: 10]; primer 17/F comprises nucleotides 3949–3970 of plasmid pDS56/RBSII,SphI-TNFα) and 21/M6 (5 -ATTGGCAGTGTTGTTCAGCCACTGGAGCTGCCCCTC-3'[SEQ ID: 13]; primer 21/M6 comprises nucleotides which are complementary to nucleotides 219–184 of plasmid pDS56/RBSII, SphI-TNFα, mutated bases are underlined). PCR reaction II was performed with primers 21/MR (5' -GCCCTCCTGGCCAATGGCGTGG-3'[SEQ ID: 14]; primer 21/MR comprises nucleotides 220–241 of plasmid pDS56/RBSII,SphI-TNFα) and 17/O (5'-CATTACTGGATCTATCAACAGG-3' [SEQ ID: 11]; primer 17/O comprises nucleotides which are complementary to nucleotides 748–727 of plasmid pDS56/RBSII,SphI-TNFα).

The resulting expression plasmid pDS56/RBSII,SphI-TNFα(Asn31Thr32) was used for production of Asn$^{31}$Thr$^{32}$-TNFα and in the construction of plasmid pDS56/RBSII,SphI-TNFα(Asn31Thr32Thr86) (see Example IV).

Example III

Preparation of Trp$^{32}$Thr$^{86}$-TNFα

Principles

For preparation of Trp$^{32}$Thr$^{86}$-TNFα the expression plasmid pDS56/RBSII,SphI-TNFα(Trp32Thr86) was constructed, which was subsequently used for the production of Trp$^{32}$Thr$^{86}$-TNFα in *E. coli*. Construction of plasmid pDS56/RBSII,SphI-TNFα(Trp32Thr86)

All the expression plasmids described in Examples I and II contain the same two sites for the restriction enzyme BglI as plasmid pDS56/RBSII,SphI-TNFα (see FIG. 1). One of these sites is located in the β-lactamase gene whereas the other site is located in the TNFα gene. This latter site separates the coding region for TNFα into two parts: one part is coding for amino acids 1 to 36 of TNFα, the other part encodes amino acids 37 to 157 of TNFα (see FIG. **1*b*1**).

For construction of plasmid pDS56/RBSII,SphI-TNFα(Trp32Thr86) DNA fragments 1 and 2 were prepared according to standard methods [Sambrook et al., 1989]. Fragment 1 (for sequences see FIG. 4) was the small BglI fragment of plasmid pDS56/RBSII,SphI-TNFα(Trp32) with the regulatable promoter and the coding region for Trp32-TNFα up to amino acid 36. Fragment 2 was the large BglI fragment of plasmid pDS56/RBSII,SphI-TNFα(Thr86) with the coding region for $Thr^{86}$-TNFα starting at amino acid 37 and the replication region of the plasmid. Fragment 1 and the enzymatically dephosphorylated fragment 2 were ligated with each other [Sambrook et al., 1989] resulting in plasmid pDS56/RBSII,SphI-TNFα(Trp32Thr86).

M15(pREP4;pDS56/RBSII,SphI-TNFα(Trp32)) cells have been deposited under the Budapest Treaty for patent purposes at the Deutsche Sammlung von Mikroorganismen und Zellkulturen GmbH (DSM) in Braunschweig, BRD at Nov. 19th, 1990 under accession number DSM 6241.

Production of $Trp^{32}Thr^{86}$-TNFα

Plasmid pDS56/RBSII,SphI-TNFα(Trp32Thr86) was transformed into *E. coli* M15 cells containing already plasmid pREP4 by standard methods [s.a.]. Transformed cells were grown at 37° C. in LB medium [s.a.] containing 100 mg/l ampicillin and 25 mg/l kanamycin. At an optical density at 600 nm of about 0.7 to 1.0 IPTG was added to a final concentration of 2 mM. After additional 2.5 to 5 h at 37° C. the cells were harvested by centrifugation.

Example IV.

Preparation of $Ser^{29}Thr^{86}$-TNFα, $Ser^{29}Trp^{32}Thr^{86}$-TNFα, $Glu^{31}Thr^{86}$-TNFα and $Asn^{31}Thr^{32}Thr^{86}$TNFα

Principles

The TNFα muteins $Ser^{29}Thr^{86}$-TNFα, $Ser^{29}Trp^{32}Thr^{86}$-TNFα, $Glu^{31}Thr^{86}$-TNFα and $Asn^{31}Thr^{32}Thr^{86}$-TNFα were prepared following the procedure described in detail in Example III for the preparation of $Trp^{32}Thr^{86}$-TNFα. Therefore, in the description of the preparation of the TNFα muteins listed above only the DNA fragments corresponding to fragment 1 of Example III are specified. Furthermore, the names of the expression plasmids encoding the various TNFα muteins are given.

Preparation of $Ser^{29}Thr^{86}$-TNFα

Fragment 1 (for sequences see FIG. 5) was the small BglI fragment of plasmid pDS56/RBSII,SphI-TNFα(Ser29) with the regulatable promoter and the coding region for $Ser^{29}$-TNFα up to amino acid 36. Fragment 1 and the enzymatically dephosphorylated fragment 2 (see Example III) were ligated with each other [Sambrook et al., 1989] resulting in plasmid pDS56/RBSII,SphI-TNFα(Ser29Thr86), which was subsequently used for the production of $Ser^{29}Thr^{86}$-TNFα in *E. coli.*

M15 (pREP4;pDS56/RBSII,SphI-TNFα(Ser29)) cells have been deposited under the Budapest Treaty for patent purposes at the Deutsche Sammlung von Mikroorganismen und Zellkulturen GmbH (DSM) in Braunschweig, BRD at Nov. 19th, 1990 under accession number DSM 6240.

Preparation of $Ser^{29}Trp^{32}Thr^{86}$-TNFα

Fragment 1 (for sequences see FIG. 6) was the small BglI fragment of plasmid pDS56/RBSII,SphI-TNFα(Ser29Trp32) with the regulatable promoter and the coding region for $Ser^{29}Trp^{32}$-TNFα up to amino acid 36. Fragment 1 and the enzymatically dephosphorylated fragment 2 (see Example III) were ligated with each other [Sambrook et al., 1989] resulting in plasmid pDS56/RBSII, SphI-TNFα(Ser29Trp32Thr86), which was subsequently used for the production of $Ser^{29}Trp^{32}Thr^{86}$-TNFα in *E. coli.*

Preparation of $Glu^{31}Thr^{86}$TNFα

Fragment 1 was the small BglI fragment of plasmid pDS56/RBSII,SphI-TNFα(Glu31) with the regulatable promoter and the coding region for $Glu^{31}$-TNFα up to amino acid 36. Fragment 1 and the enzymatically dephosphorylated fragment 2 (see Example III) were ligated with each other [Sambrook et al., 1989] resulting in plasmid pDS56/RBSII,SphI-TNFα(Glu31Thr86), which was subsequently used for the production of $Glu^{31}Thr^{86}$-TNFα in *E. coli.*

Preparation of $Asn^{31}Thr^{32}Thr^{86}$TNFα

Fragment 1 was the small BglI fragment of plasmid pDS56/RBSII,SphI-TNFα(Asn31Thr32) with the regulatable promoter and the coding region for $Asn^{31}Thr^{32}$-TNFα up to amino acid 36. Fragment 1 and the enzymatically dephosphorylated fragment 2 (see Example III) were ligated with each other [Sambrook et al., 1989] resulting in plasmid pDS56/RBSII,SphI-TNFα(Asn31Thr32Thr86), which was subsequently used for the production of Asn31Thr32Thr86-TNFα in *E. coli.*

Example V

Purification of Human TNFα Muteins

One liter overnight cultures of *E. coli* cells transformed and induced as described above were collected by centrifugation and resuspended in 20 ml 50 mM Tris, pH 7.2, 200 mM KCl, 50 mM $MgCl_2$, 5% glycerol. The cells were disrupted in a French press at a pressure of 20,000 psi. After clarification by centrifugation (70'000×g, 30 min, 4° C.) solid ammonium sulfate was added to a final concentration of 30%. The solution was stirred at room temperature for one hour and then centrifuged at 10'000×g for 20 min at 4° C. The supernatant was filtered through a 0.45 μm filter and adjusted to 70% in ammonium sulfate. The precipitated proteins were collected by centrifugation, dissolved in 20 ml 20 mM Tris, pH 9.0, and dialyzed against the same buffer overnight at 4° C. 1 ml aliquots of the dialyzed samples were applied to a MonoQ column (HR 5/5, LKB-Pharmacia) equilibrated in 20 mM Tris pH 9.0 and eluted with a linear NaCl gradient (0 to 400 mM in 20 mM Tris pH 9.0) at a flow rate of 0.5 ml/min. 0.5 ml fractions were collected and analyzed for the presence of TNFα muteins by sodium dodecyl sulfate polyacrylamide gel electrophoresis (SDS-PAGE). Positive fractions were pooled, dialyzed against 20 mM 2-morpholinoethanesulfonic acid (MES) pH 6.0 and applied to a MonoS column (HR 5/5, LKB-Pharmacia) equilibrated in 20 mM MES pH 6.0. Proteins were eluted with a linear NaCl gradient (0 to 400 mM in 20 mM MES pH 6.0) at a flow rate of 0.5 ml/min. The various TNFα muteins eluted as electrophoretically pure proteins between 250 mM and 350 mM NaCl. After dialysis against phosphate buffered saline (PBS) the protein concentration was determined by the BCA Protein Assay (Pierce Chemical Company) using wild-type human TNFα as a standard.

Example VI

Competitive Binding of Human TNFα and Muteins to Recombinant Human p75-TNF-R and p55-TNF-R For the competitive binding assay microtiter plates were coated with recombinant human p75-TNF-R-human IgGγ3 and p55-TNF-R-human IgGγ3 fusion proteins dissolved in PBS at 0.3 μg/ml and 0.1 μg/ml, respectively, (100 μl/well, overnight at 4° C.) [Loetscher, H. et al., J. Biol. Chem. 266, 18324–18329 (1991); Lesslauer, W. et al., Eur. J. Immunol. 21, 2883–2886 (1991)]. After blocking with blocking buffer (50 mM Tris pH 7.4, 140 mM NaCl, 5 mM EDTA, 0.02% $NAN_3$, 1% defatted milk powder) the microtiler plate was washed with PBS and incubated with 10 ng/ml human $^{125}$I-TNFα (labelled by the Iodogen method (Pierce Chemical Company) to a specific activity of about 30 μCi/μg) in the presence of different concentrations of the muteins. The volume was 100 μl/well and each concentration was assayed in triplicate. After three hours at room temperature the wells were thoroughly washed with PBS and counted in a g-counter.

We claim:

1. A human Tumor Necrosis Factor a mutein having selective binding affinity for the p55 subunit of human Tumor Necrosis Factor Receptor, said mutein comprising the sequence of human Tumor Necrosis Factor wherein at least one amino acid in said sequence is substituted, one of said substitutions being at position 86, wherein Thr is substituted for Ser, and said mutein having selective binding affinity for said p55 subunit of said human Tumor Necrosis Factor receptor, or a pharmaceutically acceptable salt thereof.

2. A mutein of claim 1 which is $Thr^{86}$-TNFα.

3. A mutein of claim 1 wherein the amino acid sequence is substituted at one additional position.

4. A mutein of claim 3 which is $Ser^{29}$-$Thr^{86}$-TNFα.

5. A mutein of claim 3 which is $Asp^{31}$-$Thr^{86}$-TNFα.

6. A mutein of claim 3 which is $Glu^{31}$-$Thr^{86}$-TNFα.

7. A mutein of claim 3 wherein the amino acid at position 32 is Tyr, Trp, or Thr.

8. A mutein of claim 7 which is $Thr^{32}$-$Thr^{86}$-TNFα.

9. A mutein of claim 3 which is $Trp^{32}$-$Thr^{86}$-TNFα.

10. A mutein of claim 1 wherein the amino acid sequence is substituted at two additional positions.

11. A mutein of claim 10 which is $Ser^{29}$-$Trp^{32}$-$Thr^{86}$-TNFα.

12. A mutein of claim 10 which is $Asn^{31}$-$Thr^{32}$-$Thr^{86}$-TNFα.

13. A polynucleotide comprising a coding DNA sequence which encodes the mutein of claim 1 or the DNA sequence complementary to said coding DNA sequence.

14. A polynucleotide comprising a coding DNA sequence which encodes the mutein of claim 2 or the DNA sequence complementary to said coding DNA sequence.

15. A polynucleotide comprising a coding DNA sequence which encodes the mutein of claim 3 or the DNA sequence complementary to said coding DNA sequence.

16. A polynucleotide comprising a coding DNA sequence which encodes the mutein of claim 4 or the DNA sequence complementary to said coding DNA sequence.

17. A polynucleotide comprising a coding DNA sequence which encodes the mutein of claim 5 or the DNA sequence complementary to said coding DNA sequence.

18. A polynucleotide comprising a coding DNA sequence which encodes the mutein of claim 6 or the DNA sequence complementary to said coding DNA sequence.

19. A polynucleotide comprising a coding DNA sequence which encodes the mutein of claim 7 or the DNA sequence complementary to said coding DNA sequence.

20. A polynucleotide comprising a coding DNA sequence which encodes the mutein of claim 8 or the DNA sequence complementary to said coding DNA sequence.

21. A polynucleotide comprising a coding DNA sequence which encodes the mutein of claim 9 or the DNA sequence complementary to said coding DNA sequence.

22. A polynucleotide comprising a coding DNA sequence which encodes the mutein of claim 10 or the DNA sequence complementary to said coding DNA sequence.

23. A polynucleotide comprising a coding DNA sequence which encodes the mutein of claim 11 or the DNA sequence complementary to said coding DNA sequence.

24. A polynucleotide comprising a coding DNA sequence which encodes the mutein of claim 12 or the DNA sequence complementary to said coding DNA sequence.

25. A vector capable of causing expression in a prokaryotic or lower eukaryotic host cell of a polynucleotide comprising the coding DNA sequence of claim 24.

26. A host cell transformed with a vector of claim 25.

27. A host cell of claim 26 which is *E. coli.*

* * * * *